United States Patent
Dalvi et al.

(10) Patent No.: US 12,318,176 B2
(45) Date of Patent: Jun. 3, 2025

(54) SYSTEMS AND METHODS FOR MEASURING BLOOD PRESSURE

(71) Applicant: MASIMO CORPORATION, Irvine, CA (US)

(72) Inventors: Cristiano Dalvi, Lake Forest, CA (US); Marcelo M. Lamego, Cupertino, CA (US); Massi Joe E. Kiani, Laguna Niguel, CA (US); Jeroen Poeze, Rancho Santa Margarita, CA (US); Hung The Vo, Fountain Valley, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/592,189

(22) Filed: Feb. 29, 2024

(65) Prior Publication Data
US 2024/0277240 A1    Aug. 22, 2024

Related U.S. Application Data

(63) Continuation of application No. 17/191,052, filed on Mar. 3, 2021, now Pat. No. 11,944,415, which is a
(Continued)

(51) Int. Cl.
*A61B 5/0235* (2006.01)
*A61B 5/022* (2006.01)
(Continued)

(52) U.S. Cl.
CPC ........ *A61B 5/0235* (2013.01); *A61B 5/02233* (2013.01); *F16K 1/302* (2013.01); *F16K 1/303* (2013.01); *F16K 13/04* (2013.01)

(58) Field of Classification Search
None
See application file for complete search history.

(56) References Cited

U.S. PATENT DOCUMENTS

| 2,717,100 A | 9/1955 | Engelder |
| 2,974,503 A | 3/1961 | Newton |

(Continued)

FOREIGN PATENT DOCUMENTS

| GB | 948 351 | 1/1964 |
| WO | WO 2007/137347 | 12/2007 |

(Continued)

OTHER PUBLICATIONS

US 2024/0016391 A1, 01/2024, Lapotko et al. (withdrawn)
Advanced/Deluxe One Step Auto-Inflation Blood Pressure Monitor Model UA-767 Plus. User guide[online]. Life Source, 2009 [retrieved on Apr. 28, 2016]. Retrieved from internet <https://www.andonline.com/uploads/documents/I-MAN-UA-767PV_0409.pdf>.

(Continued)

*Primary Examiner* — Jay B Shah
(74) *Attorney, Agent, or Firm* — Knobbe, Martens, Olson & Bear, LLP

(57) ABSTRACT

A blood pressure measurement system is provided that includes an inflatable cuff, a valve assembly and chamber assembly. The chamber assembly can house a gas canister for providing gas to the inflatable cuff. The valve assembly can include a valve having a high pressure cavity, a low pressure cavity, and a channel providing a gas pathway between the high pressure cavity and the low pressure cavity. The valve assembly can further include a channel cover and spring in the high pressure cavity. The spring can exert a force on the channel cover to create a seal between the high pressure cavity and the channel. The valve assembly can further include a rod extending through the channel and exerting a force on the channel cover to create a gas pathway between the high pressure cavity and the channel.

19 Claims, 23 Drawing Sheets

Related U.S. Application Data continuation of application No. 16/381,516, filed on Apr. 11, 2019, now Pat. No. 10,980,432, which is a continuation of application No. 14/450,030, filed on Aug. 1, 2014, now Pat. No. 10,555,678.

(60) Provisional application No. 61/933,681, filed on Jan. 30, 2014, provisional application No. 61/862,223, filed on Aug. 5, 2013.

(51) Int. Cl.
*F16K 1/30* (2006.01)
*F16K 17/40* (2006.01)

(56) References Cited

U.S. PATENT DOCUMENTS

| | | |
|---|---|---|
| 3,316,395 A | 4/1967 | Lavin |
| 3,316,396 A | 4/1967 | Trutt et al. |
| 4,163,290 A | 7/1979 | Sutherlin et al. |
| 4,305,059 A | 12/1981 | Benton |
| 4,491,725 A | 1/1985 | Pritchard |
| 4,800,892 A | 1/1989 | Perry et al. |
| 4,800,982 A | 1/1989 | Perry et al. |
| 4,889,132 A | 12/1989 | Hutcheson et al. |
| 4,960,128 A | 10/1990 | Gordon et al. |
| 4,964,408 A | 10/1990 | Hink et al. |
| 4,973,024 A | 11/1990 | Homma |
| 5,041,187 A | 8/1991 | Hink et al. |
| 5,069,213 A | 12/1991 | Hink et al. |
| 5,163,438 A | 11/1992 | Gordon et al. |
| 5,234,015 A | 8/1993 | Fumino |
| 5,319,355 A | 6/1994 | Russek |
| 5,337,744 A | 8/1994 | Branigan |
| 5,341,805 A | 8/1994 | Stavridi et al. |
| 5,377,676 A | 1/1995 | Vari et al. |
| 5,392,781 A | 2/1995 | Phillipps et al. |
| 5,431,170 A | 7/1995 | Mathews |
| 5,436,499 A | 7/1995 | Namavar et al. |
| 5,449,379 A | 9/1995 | Hadtke |
| 5,452,717 A | 9/1995 | Branigan et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,560,366 A | 10/1996 | Harada et al. |
| 5,590,649 A | 1/1997 | Caro et al. |
| 5,590,662 A | 1/1997 | Hersh et al. |
| 5,590,696 A | 1/1997 | Phillips et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,045,510 A | 4/2000 | Ogura |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,152 A | 7/2000 | Patterson |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,328,280 B1 | 12/2001 | Davidson |
| 6,334,065 B1 | 12/2001 | Al-Ali et al. |
| 6,336,901 B1 | 1/2002 | Itonaga et al. |
| 6,343,224 B1 | 1/2002 | Parker |
| 6,349,228 B1 | 2/2002 | Kiani et al. |
| 6,358,212 B1 | 3/2002 | Hasegawa et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,405,943 B1 | 6/2002 | Stadnyk |
| 6,411,373 B1 | 6/2002 | Garside et al. |
| 6,415,167 B1 | 7/2002 | Blank et al. |
| 6,420,186 B1 | 7/2002 | Berger et al. |
| 6,430,437 B1 | 8/2002 | Marro |
| 6,430,525 B1 | 8/2002 | Weber et al. |
| 6,450,966 B1 | 9/2002 | Hanna |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |

(56) References Cited

U.S. PATENT DOCUMENTS

| | | |
|---|---|---|
| 6,541,756 B2 | 4/2003 | Schulz et al. |
| 6,542,764 B1 | 4/2003 | Al-Ali et al. |
| 6,543,444 B1 | 4/2003 | Lewis |
| 6,565,524 B1 | 5/2003 | Itonaga et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| 6,697,878 B1 | 2/2004 | Imai |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,843,465 B1 | 1/2005 | Scott |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,988,992 B2 | 1/2006 | Just et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,878 B2 | 2/2006 | Inagaki et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,153,269 B1 | 12/2006 | Blansett |
| 7,166,076 B2 | 1/2007 | Poliac et al. |
| 7,186,218 B2 | 3/2007 | Hersh et al. |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,311,670 B2 | 12/2007 | Just et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |

(56) References Cited

U.S. PATENT DOCUMENTS

| | | |
|---|---|---|
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al-Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,678,057 B2 | 3/2010 | Berkow et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-All et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |

(56) References Cited

U.S. PATENT DOCUMENTS

| | | |
|---|---|---|
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Klani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Klani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |

(56) References Cited

U.S. PATENT DOCUMENTS

| | | |
|---|---|---|
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,919 B2 | 6/2018 | Lamego et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |

(56) References Cited

U.S. PATENT DOCUMENTS

| | | |
|---|---|---|
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,980,432 B2 | 4/2021 | Dalvi et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Klani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,944,415 B2 | 4/2024 | Dalvi et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0125609 A1 | 7/2003 | Becker |
| 2003/0144582 A1 | 7/2003 | Cohen et al. |
| 2003/0156288 A1 | 8/2003 | Barnum et al. |
| 2003/0205578 A1 | 11/2003 | Newport |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0056747 A1 | 3/2005 | Belcourt et al. |
| 2005/0234317 A1 | 10/2005 | Kiani |
| 2005/0288571 A1 | 12/2005 | Perkins et al. |
| 2005/0288597 A1 | 12/2005 | Kishimoto et al. |
| 2006/0036751 A1 | 2/2006 | Garbow |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0211923 A1 | 9/2006 | Al-Ali et al. |
| 2007/0073116 A1 | 3/2007 | Kiani et al. |
| 2007/0073173 A1 | 3/2007 | Lam et al. |
| 2007/0180140 A1 | 8/2007 | Welch et al. |
| 2007/0221056 A1 | 9/2007 | Kutella |
| 2007/0244363 A1 | 10/2007 | Sano et al. |
| 2007/0244377 A1 | 10/2007 | Cozad et al. |
| 2007/0276263 A1 | 11/2007 | Eide |

(56) References Cited

U.S. PATENT DOCUMENTS

| | | |
|---|---|---|
| 2007/0282478 A1 | 12/2007 | Al-Ali et al. |
| 2007/0287923 A1 | 12/2007 | Adkins et al. |
| 2008/0001735 A1 | 1/2008 | Tran |
| 2008/0045846 A1 | 2/2008 | Friedman et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2008/0236586 A1 | 10/2008 | McDonald et al. |
| 2008/0287814 A1 | 11/2008 | Muehsteff et al. |
| 2008/0294455 A1 | 11/2008 | Bharara |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0126482 A1 | 5/2009 | Dundak et al. |
| 2009/0194718 A1 | 8/2009 | Kulesha |
| 2009/0198302 A1 | 8/2009 | Anderson et al. |
| 2009/0234381 A1 | 9/2009 | Karo |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0050085 A1 | 2/2010 | Blike |
| 2010/0099964 A1 | 4/2010 | O'Reilly et al. |
| 2010/0137725 A1 | 6/2010 | Takahashi |
| 2010/0211096 A1 | 8/2010 | McEwen et al. |
| 2010/0234698 A1 | 9/2010 | Manstrom et al. |
| 2010/0234718 A1 | 9/2010 | Sampath et al. |
| 2010/0270257 A1 | 10/2010 | Wachman et al. |
| 2011/0009757 A1 | 1/2011 | Sano et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0066009 A1 | 3/2011 | Moon et al. |
| 2011/0082711 A1 | 4/2011 | Poeze et al. |
| 2011/0087081 A1 | 4/2011 | Kiani et al. |
| 2011/0092827 A1 | 4/2011 | Hu et al. |
| 2011/0105854 A1 | 5/2011 | Kiani et al. |
| 2011/0112412 A1 | 5/2011 | Sano et al. |
| 2011/0118561 A1 | 5/2011 | Tari et al. |
| 2011/0118613 A1 | 5/2011 | Yokoyama et al. |
| 2011/0125060 A1 | 5/2011 | Telfort et al. |
| 2011/0137297 A1 | 6/2011 | Kiani et al. |
| 2011/0152785 A1 | 6/2011 | Chattaraj et al. |
| 2011/0166459 A1 | 7/2011 | Kopetsch et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2011/0237962 A1 | 9/2011 | Hersh et al. |
| 2011/0257539 A1 | 10/2011 | Sawanol |
| 2012/0041276 A1 | 2/2012 | Doreus et al. |
| 2012/0059267 A1 | 3/2012 | Lamego |
| 2012/0123231 A1 | 5/2012 | O'Reilly |
| 2012/0157791 A1 | 6/2012 | Hersh |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0232416 A1 | 9/2012 | Gilham et al. |
| 2012/0240377 A1 | 9/2012 | Ashida |
| 2012/0283524 A1 | 11/2012 | Kiani et al. |
| 2012/0316449 A1 | 12/2012 | Uesaka et al. |
| 2012/0319816 A1 | 12/2012 | Al-Ali |
| 2012/0330112 A1 | 12/2012 | Lamego et al. |
| 2012/0330169 A1 | 12/2012 | Sano et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0060153 A1 | 3/2013 | Kobayashi et al. |
| 2013/0096405 A1 | 4/2013 | Garfio |
| 2013/0096936 A1 | 4/2013 | Sampath et al. |
| 2013/0138000 A1 | 5/2013 | Kinoshita et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |

(56) References Cited

U.S. PATENT DOCUMENTS

| | | |
|---|---|---|
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Klani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhshin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0221966 A1 | 7/2019 | Kiani et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Klant et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali et al. |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Klani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |

(56) References Cited

U.S. PATENT DOCUMENTS

| | | |
|---|---|---|
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0252046 A1 | 8/2024 | Jansen et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |

FOREIGN PATENT DOCUMENTS

| | | |
|---|---|---|
| WO | WO 2009/153710 | 12/2009 |
| WO | WO 2013/170095 | 11/2013 |
| WO | WO 2015/020911 | 2/2015 |

OTHER PUBLICATIONS

Bureau of Indian Standards: "Fire Extinguisher, Carbon Dioxide Type (Portable and Trolley Mounted)—Specification." Aug. 1, 2004, retrieved from the internet: https://law.resource.org/pub/in/bis/S03/is.2878.2004.html.

Innovations Ultraflate Plus: https://www.youtube.com/watch?v=nUcx-e91zz0. (1 page).

Innovations Ultraflate Plus CO2 Amazon customer review, Mar. 2008: http://www.amazon.com/Genuine-Innovations-2425-Ultraflate-Plus/product-reviews/B00278XO0Q. (4 pages).

International Search Report and Written Opinion received in PCT Application No. PCT/US2013/040438, dated Jul. 26, 2013.

International Search Report and Written Opinion received in PCT Application No. PCT/US2014/049490, dated Mar. 31, 2015.

International Preliminary Report on Patentability and Written Opinion received in PCT Application No. PCT/US2013/040438, dated Nov. 20, 2014.

International Preliminary Report on Patentability and Written Opinion received in PCT Application No. PCT/US2014/049490, dated Feb. 18, 2016.

Invitation to Pay Fees received in PCT Application No. PCT/US2014/049490, dated Nov. 26, 2014.

Jun Onoderan, Validation of Infationary non-invasive blood pressure monitoring in adult surgical patients, Journal of Anesthesiology, 2011, vol. 25, pp. 127-130.

Osamu Tochikubo, A New Portable Device for Recording 24-h Indirect Blood Pressure in Hypertensive Outpatients, Journal of Hypertension, 1985, vol. 3, pp. 335-357.

Ultraflate: http://www.genuineinnovations.com/us/products/inflators/ultraflate.php. (2 pages).

SYSTEMS AND METHODS FOR MEASURING BLOOD PRESSURE

RELATED APPLICATIONS

The present application is a continuation of U.S. application Ser. No. 17/191,052, filed Mar. 3, 2021, which is a continuation of U.S. application Ser. No. 16/381,516, filed Apr. 11, 2019, which is a continuation of U.S. application Ser. No. 14/450,030, filed Aug. 1, 2014, which claims the benefit of U.S. Provisional Application No. 61/862,223, filed Aug. 5, 2013, and U.S. Provisional Application No. 61/933,681, filed Jan. 30, 2014, each of which is hereby incorporated herein by reference in its entirety.

BACKGROUND

Blood pressure monitoring is an important indicator of a wearer's cardiovascular status. Many devices allow blood pressure to be measured by manual or digital sphygmomanometer systems that utilize an inflatable cuff applied to a person's arm. These devices often include an inflatable cuff to restrict blood flow and a device capable of measuring the pressure.

In a typical blood pressure monitoring system, a hand actuated pump or an electric motor inflates the inflatable cuff to a pressure level at or above the expected systolic pressure of the wearer and high enough to occlude an artery. Automated or motorized blood pressure monitoring systems use a motor or pump to inflate the inflatable cuff, while manual blood pressure monitors typically use an inflation bulb. As the air from the inflatable cuff is slowly released, the wearer's blood pressure can be determined by detecting Korotkoff sounds using a stethoscope or other detection device placed over an artery.

However, both systems have their drawbacks. For example, these systems can cause pain or discomfort to the wearer. Other adverse effect can include limb edema, venous stasis, peripheral neuropathy, etc., or simply wearer interruption. In addition, manual systems make it difficult to measure blood pressure during inflation of the inflatable cuff due to the difficult of inflating the inflatable cuff at an approximately constant rate using an inflation bulb. Furthermore, motorized blood pressure monitors are often noisy and can disturb wearers at rest. In addition to auditory noise in automated or motorized systems, the motors can cause electrical noise in sensor signals making signal processing used to identify reference points for blood pressure detection unreliable and difficult.

Gas canisters, which are frequently used to supply gas in a fast and efficient manner, can be used in place of the motor and pump. However, due to the relatively high pressure of the gas inside the gas canister, care must be used when puncturing the seal of the gas canister to allow the gas to exit. To alleviate this danger, the nozzle of many gas canisters are threaded to engage with a complementary threaded release valve. A user inserts the nozzle of the gas canister into the release valve and then rotates the gas canister to engage the threads. Once the gas canister is sufficiently screwed into the release valve, a sharp point of the release valve punctures the top of the canister and allows the gas to exit.

However, there are several drawbacks to this approach. For example, the threads of the gas canister or the release valve may be stripped or may not align properly. In addition, the gas canister is left exposed, and a user may unwittingly unscrew a partially filled gas canister from the release valve. Furthermore, once punctured, many release valves do not provide any mechanism for controlling, or stopping, the flow of gas.

DETAILED DESCRIPTION

As described herein, a valve-chamber assembly is provided that allows a user to place a gas canister in a chamber assembly, close the cover, and engage the gas canister with a valve assembly. In some embodiments, the valve-chamber assembly can provide a user with the ability to control and change the flow rate of the gas exiting the gas canister. In certain embodiments, the valve-chamber assembly can be used in conjunction with a blood pressuring monitoring system, such as the one described in greater detail in U.S. application Ser. No. 13/838,225 filed Mar. 15, 2013 (the '225 application), incorporated herein by reference for all purposes. In such embodiments, the valve-chamber assembly can be coupled with any one or more of the gas pathways and/or gas pathway segments described in the '225 application (e.g., gas pathways 124 and/or gas pathway segments 210, 214, 218). In some embodiments, the valve-chamber assembly can be used in place of the chamber 306 described in the '225 application.

For simplicity, as used herein, an upward direction refers to the direction from the chamber assembly to the valve assembly, and an upward force refers to a force from the direction of the chamber assembly to the valve assembly. Similarly, a downward direction refers to the direction from the valve assembly to the chamber assembly, and a downward force refers to a force in the direction from the valve assembly to the chamber assembly. However, it will be understood that "upward," the "upward force," "downward," and/or the "downward force" may be directed upwards, downwards, laterally, or any combination thereof.

Blood Pressure Monitoring System

Figure 1A:
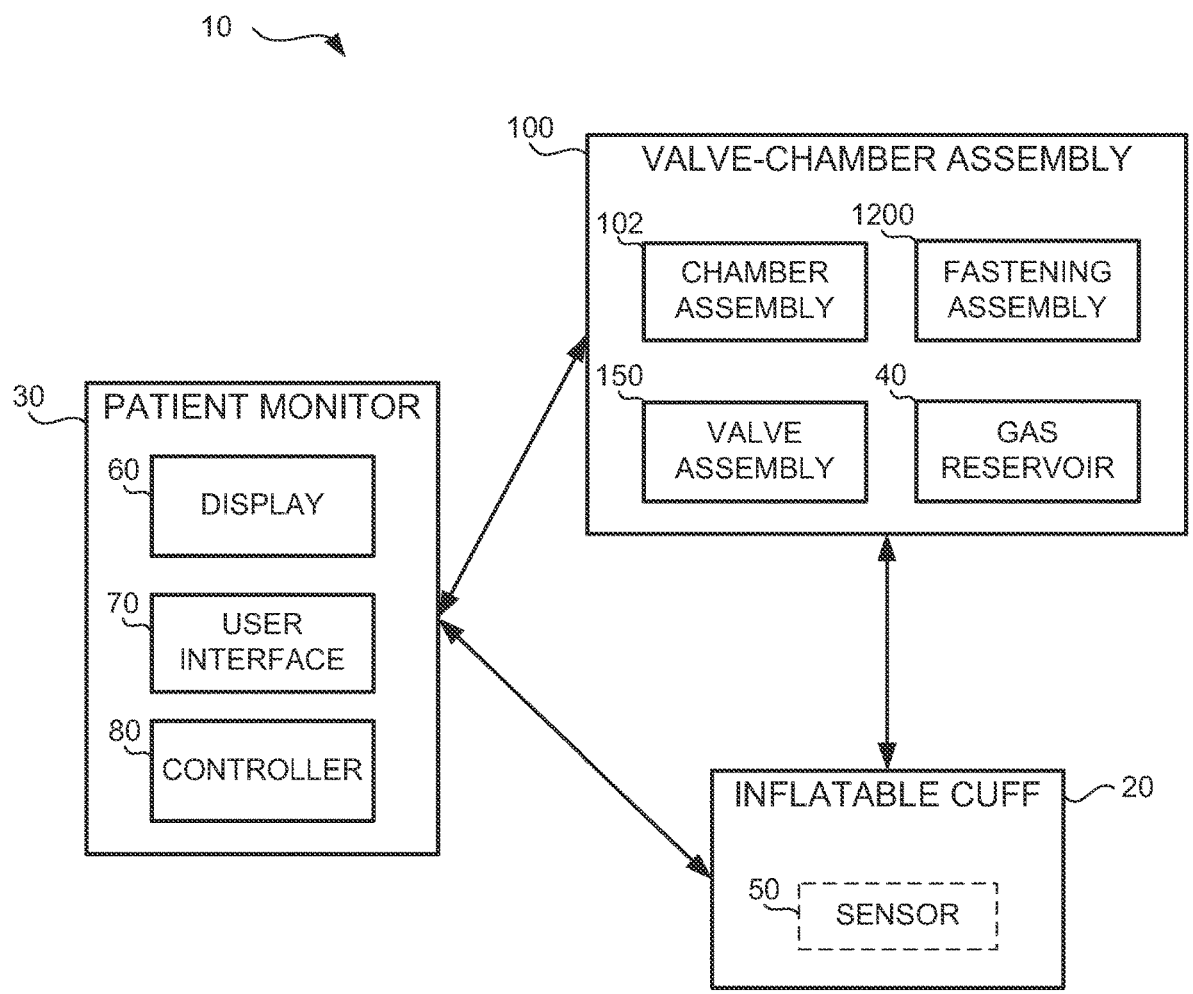
FIG. 1A is a block diagram illustrating an embodiment of a patient monitoring system.

FIG. 1A is a block diagram illustrating an embodiment of a blood pressure monitoring system 10. The blood pressure monitoring system 10 can be used to measure the blood pressure of a wearer during inflation, deflation or both. In the illustrated embodiment, the blood pressure monitoring system 10 includes an inflatable cuff 20, a valve-chamber assembly 100, and a patient monitor 30. However, it will be understood that the blood pressure monitoring system 10 can include fewer or more components as desired.

The inflatable cuff 20 can be used to at least partially obstruct the flow of blood through a wearer's artery in order to measure the wearer's blood pressure, and can include a bladder that can be filled with gas in a manner controlled by a user and/or the patient monitor 30. The inflatable cuff 20 can receive the gas for inflation from a gas reservoir 40 via a gas pathway. However, in some cases, a motor can be used to inflate the inflatable cuff 20 as desired. In some embodiments, the inflatable cuff 20 can be a disposable cuff that can be discarded after a one or a few uses. In certain embodiments, the inflatable cuff 20 can be reused many times and cleaned or sterilized between uses.

In use, the inflatable cuff 20 can be attached to a wearer's arm or other location, and can be inflated automatically (e.g., via intelligent cuff inflation) or manually to obtain blood pressure data. Blood pressure data can include any type of signal received from a sensor sufficiently responsive to blood pressure to provide an indicator thereof to a user. Blood pressure data can be in the form of pressure sensor data, auditory sensor data, and the like.

The inflatable cuff 20 can also include a release valve for releasing the gas stored therein once inflated. The release valve can be actuated electronically by the patient monitor 30 or manually by a user. In some embodiments, the release valve can be used when the pressure in the inflatable cuff 20 reaches unsafe levels or when the inflatable cuff 20 has been inflated beyond a threshold period of time. In certain embodiments, the release valve can be actuated electronically using PWM signals.

The inflatable cuff 20 can further include a wireless transmitter for wireless communication with the patient monitor 30 and/or valve-chamber assembly 100. In some embodiments, the inflatable cuff can include cables for sending and receiving information to and from the patient monitor 30 and/or valve-chamber assembly 100.

A sensor 50 can be placed in close proximity to the inflatable cuff 20 to monitor the inflatable cuff 20 during inflation and deflation. Alternatively, the sensor 50 can be located in the patient monitor 30 along a gas pathway between the gas reservoir 40 and inflatable cuff 20, or at some other location where it is able to collect sufficient data for the patient monitor 30 to determine the blood pressure of the wearer.

The sensor 50 can be a pressure sensor or an auditory sensor. In some embodiments, the sensor 50 can communicate signals responsive to the pressure in the inflatable cuff 20 to the patient monitor 30 via wired or wireless communication. The patient monitor can use the signal to determine a blood pressure measurement or change in blood pressure of the wearer. The patient monitor 30 can additionally use the pressure measurements to determine if the pressure in the inflatable cuff 20 is above a threshold or is at an unsafe level. If the pressure in the inflatable cuff 20 is above a threshold or is at an unsafe level, the patient monitor 30 can actuate an emergency release valve to deflate the inflatable cuff 20. In an embodiment where the sensor 50 is an auditory sensor, the sensor 50 can be used to detect Korotkoff sounds. In some cases, the sensor 50 be implemented using a stethoscope.

With continued reference to FIG. 1A, the patient monitor 30 can include a display 60, a user interface 70, and a controller 80. The display 60 can be implemented using a touch screen, LCD screen, LED screen, or other type of screen and can be used to display one or more physiological parameters, plot diagrams, or user interface information, etc.

The display 60 can be any number of different sizes, and in some embodiments, covers a majority of one side of the patient monitor 30. The controller 80 can be implemented using a microprocessor, microcontroller, programmable logic device (PLD), field programmable gate array (FPGA), and the like.

The patient monitor 30 can further include a number of components implemented by the controller 80 for filtering the blood pressure data received from the sensor 50 and determining the blood pressure of the wearer. The patient monitor 30 can be a dedicated device for determining blood pressure and other physiological parameters, a portable electronic device configured to execute a program or application that determines blood pressure and other physiological parameters, or can be part of a larger patient monitoring device, such as those devices described in U.S. patent application Ser. No. 09/516,110, titled "Universal Upgrading Pulse Oximeter," filed Mar. 1, 2000 (MASIMO.162C1); U.S. patent application Ser. No. 12/534,827, titled "Multi-Stream Data Collection System For Noninvasive Measurement Of Blood Constituents," filed Aug. 3, 2009 (MLHUM.002A); U.S. patent application Ser. No. 12/497,523, titled "Contoured Protrusion For Improving Spectroscopic Measurement Of Blood Constituents," filed Jul. 2, 2009 (MLHUM.007A); U.S. patent application Ser. No. 12/882,111, titled "Spot Check Monitor Credit System," filed Sep. 14, 2010 (MLHUM.022A); U.S. patent application Ser. No. 13/308,461, titled "Handheld Processing Device Including Medical Applications For Minimally And Non Invasive Glucose Measurements," filed Nov. 30, 2011 (MLHUM.039A) and U.S. patent application Ser. No. 11/366,995, titled "Multiple Wavelength Sensor Equalization," filed Mar. 1, 2006 (MLR.003A). Each of which is incorporated by reference herein.

In some embodiments, the patient monitor 30 can communicate with the inflatable cuff 20 and/or the gas reservoir 40 via wired or wireless communication, such as LAN, WAN, Wi-Fi, infra-red, Bluetooth, radio wave, cellular, or the like, using any number of communication protocols. The patient monitor 30 can further be configured to determine blood pressure measurements of a wearer when the inflatable cuff 20 inflating, deflating, or a combination of both. The patient monitor 30 can use the controller 80 to determine the blood pressure measurements. The blood pressure measurements determined by the patient monitor 30 can be displayed on the display 60. In addition, the display 60 can display blood pressure data and filtered blood pressure data in the form of plots of the pressure of the inflatable cuff and plots of the pressure oscillations in the inflatable cuff 20 caused by blood flowing through an artery of the wearer. Furthermore, the patient monitor 30 can calculate and the display 60 can display additional physiological parameters, such as heart rate, perfusion, oxygen saturation, respiration rate, activity information, temperature, and the like, combinations thereof or the trend of any of the above.

The user interface 70 can enable a user to operate the patient monitor 30 and obtain the blood pressure measurements and/or other physiological parameters. Furthermore, the user interface 70 can enable a user to set or change any number of configuration parameters. For example, using the user interface 70, a user can determine what to display on the display 60, such as the blood pressure measurements during inflation and/or deflation, additional physiological parameters, the pressure plots, and/or other physiological parameters, etc.

With continued reference to FIG. 1A, the valve-chamber assembly 100 can include a chamber assembly 102, a valve assembly 150, a fastening assembly 1200, and a gas reservoir 40. Embodiments of the chamber assembly 102 are described in greater detail below with reference to FIGS. 2-10. Embodiments of the valve assembly 150 are described in greater detail below with reference to FIGS. 2-10 and 15A-15E. Embodiments of the fastening assembly 1200 are described in greater detail below with reference to FIGS. 13 and 14A-14D.

The gas reservoir 40 can house compressed gas and can be operatively coupled to the inflatable cuff 20 via a gas pathway. As will be described in greater detail below with reference to FIGS. 2-10 and 15A-15E, in some embodiments, the valve assembly 150 can be located in the gas pathway between the inflatable cuff 20 and the gas reservoir 40. The valve assembly 150 can provide a desired pressure or flow in the inflatable cuff so long as there is sufficient gas in the reservoir 40. Accordingly, gas can flow from the gas reservoir 40, through the valve assembly 150 to the bladder of the inflatable cuff 20. In some embodiments, the gas pathway can be an airtight pathway constructed of any number of materials including, but not limited to, metal, plastic, cloth, combinations of the same or some other airtight material.

The gas reservoir 40 can be implemented using one or more disposable or reusable gas tanks, cylinders, bottles, canisters, or cartridges, of any number of shapes or sizes, and can be located in the same room as the wearer, or can be remotely located from the wearer, such as in a different room or even in a different building. For example, the gas reservoir 40 can include a large gas tank that remains in a stationary location. The gas reservoir 40 can be large enough to contain sufficient gas for a large number of blood pressure readings (e.g. more than 100). Furthermore, the gas reservoir 40 can store compressed gas at any number of PSI levels. For example, the gas reservoir can store compressed gas up to about 6000 PSI or more, depending on the safety conditions of the environment. Furthermore, the gas tank can be configured to supply gas to multiple inflatable cuffs 20, thereby limiting the number of gas tanks used for multiple wearers. When the pressure levels in the gas tank reach a threshold, the gas tank can either be refilled, replaced or a combination of both. For example a rotating cache of gas tanks can be used as the gas reservoir 40.

Alternatively, the gas reservoir 40 can be implemented using a small gas tank of any number of sizes. For example, the gas reservoir 40 can be implemented using a gas tank that is small enough to fit in the palm of a hand, such as a carbon dioxide ($CO_2$) cartridges similar to or the same as those used for paint ball guns, tire inflation, or the like. $CO_2$ cartridges are available from a number of different manufacturers and distributors, such as the AirSource 88 Gram Pre-filled Disposable $CO_2$ cartridge available from Crosman (Product Code: CRO-88-GRAM). The PSI levels for smaller gas tanks can also differ greatly and can store compressed gas up to about 2000 PSI or more. In certain embodiments, the gas reservoir 40 can be implemented using a gas tank of compressed gas at about 1000 PSI.

Smaller gas reservoirs 40 can be used where mobility is desired. For example, paramedics or first responders can carry a small gas reservoir 40 for measuring blood pressure of persons needing emergency medical care. Using the gas reservoir 40, the emergency personnel (or some other user) can measure the blood pressure of the wearer during inflation of the inflatable cuff, deflation, or a combination of the two. The measurements can be taken using a patient monitor 30, manually using a stethoscope, or other methods.

In some embodiments, a pressure regulator, or the valve assembly 150, can be placed at an opening of the gas reservoir 40 and can control whether gas exits the gas reservoir and the amount of gas allowed to exit. The valve assembly 150 can also be configured to control the rate at which gas flows to the inflatable cuff 20, as well as the pressure of the gas or PSI level.

Using the valve assembly 150, the inflatable cuff 20 can be inflated at a controlled rate, such as, for example, an approximately constant rate or linear rate. By inflating the inflatable cuff at a controlled rate, the wearer's blood pressure can be measured during inflation and without occluding the artery. In some embodiments, the valve assembly 150 can further include a wireless transmitter for communication with the patient monitor 30, which in turn may electronically control and/or monitor the flow of gas through the valve assembly 150. Alternatively, the valve assembly 150 can communicate with the patient monitor 30 via wired communication.

Additionally, in some embodiments, the gas reservoir 40 can include a pressure gauge to monitor the remaining pressure and/or the amount of compressed gas remaining in the gas reservoir 40. The pressure gauge can communicate the pressure levels to the patient monitor 30 via wired or wireless communication, similar to the valve assembly 150. Once the pressure gauge indicates a threshold pressure level or gas level has been reached, the patient monitor 30 can indicate that the gas reservoir 40 should be replaced or refilled.

The gas reservoir 40 can contain any number of compressed gases to inflate the inflatable cuff 20. For example, the gas reservoir 40 can contain compressed air, carbon dioxide, nitrogen, oxygen, helium, hydrogen, etc. Any number of other gases can be used to inflate the inflatable cuff 20. Furthermore, the gas reservoir 40 may house enough gas to inflate the inflatable cuff 20 without the use of a motor or pump during the inflation.

The gas reservoir 40 can be pre-filled with gas near the wearer or at a remote site away from the wearer. In one embodiment, the gas reservoir 40 is filled with gas prior to being associated with the inflatable cuff 20. Pre-filling the gas reservoir 40 prior to use can significantly reduce the ambient noise caused during inflation of the inflatable cuff 20. In addition, by using the gas reservoir 40, the electrical noise from a motor can be removed. The reduction in ambient and electrical noise and the approximately constant rate of inflation of the inflatable cuff 20 allows the patient monitor 30 to measure the wearer's blood pressure while the inflatable cuff 20 is inflating. In addition, the gas reservoir 40 can be used to quickly inflate the inflatable cuff 20 for blood pressure measurements taken during deflation of the inflatable cuff 20.

In some embodiments, multiple gas reservoirs 40 can be included as part of the blood pressure monitoring system 10. The multiple gas reservoirs 40 can be used for backup purposes or for different tasks. For example, a first gas reservoir 40 can be a large gas reservoir and can be used to supply gas to the inflatable cuff 20 when the user is stationary. A second optionally smaller gas reservoir 40 can also be provided. When the user moves away from the first gas reservoir 40, the first gas reservoir can be disconnected from the inflatable cuff 20 and the second gas reservoir 40 will supply the gas to the inflatable cuff 20. In certain embodiments, a pump may be connected to the inflatable cuff 20 and used when the user is stationary. When the user moves, the pump is disconnected and the gas reservoir 40 supplies the gas to the inflatable cuff 20.

In certain embodiments the gas reservoir 40 can include an identifier that identifies the gas reservoir 40 to the patient monitor 30. The identifier can be implemented using one or more memory chips or RFIDS located on the gas reservoir and/or one or more circuit elements, such as resistors, capacitors, inductors, op-amps, etc. The identifier can include additional information regarding the gas reservoir 40, such as the type of gas reservoir, manufacturing date and/or location, storage capacity or amount of gas that the gas reservoir 40 can hold, the quantity of gas in the gas reservoir, PSI levels, usage data, expiration dates, product histories, etc.

The patient monitor 30 can use the identifier to determine whether to use the gas reservoir 40, whether the gas reservoir 40 is compatible with the patient monitor 30, or whether the gas reservoir 40 is from an authorized supplier. The identifier can be unique for each gas reservoir 40 or for a set of gas reservoirs 40. In some embodiments, the identifier indicates that the gas reservoir can be used with the patient monitor 30. In certain embodiments, only gas reservoirs 40 with a particular identifier are used with the patient monitor 30. Accordingly, gas reservoirs 40 that do not include the particular identifier can be rejected and/or ignored by the patient monitor 30. In an embodiment, an emergency use override may allow for measurements, or a specific number of measurements in an emergency situation, even when, for example, the identifier does not indicate an authorized supplier but is otherwise safe for use.

It is to be understood that other techniques exist for implementing the gas reservoir 40 without departing from the spirit and scope of the description. For example, the gas reservoir 40 can be implemented using the central gas line of a building, such as a hospital or other healthcare facility. Alternatively, the gas reservoir 40 can be implemented using a bulb, bladder, pump, or the like. In still further embodiments, the foregoing alternatives may serve as backup options if the gas reservoir 40 is empty or otherwise not functional.

Figure 1B:
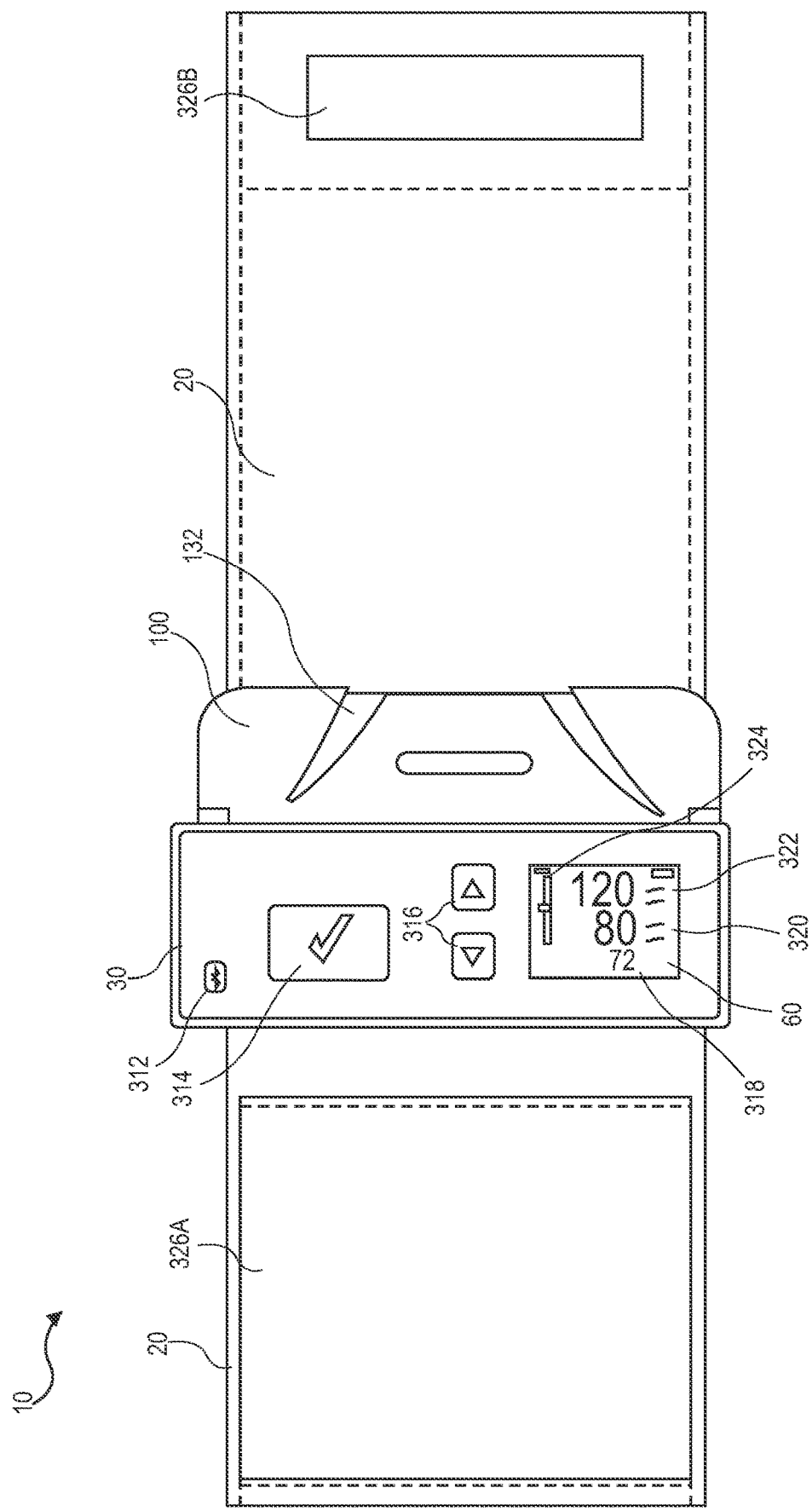
FIG. 1B is a drawing illustrating an embodiment of a patient monitoring system configured to be worn by a user.
Figure 2:
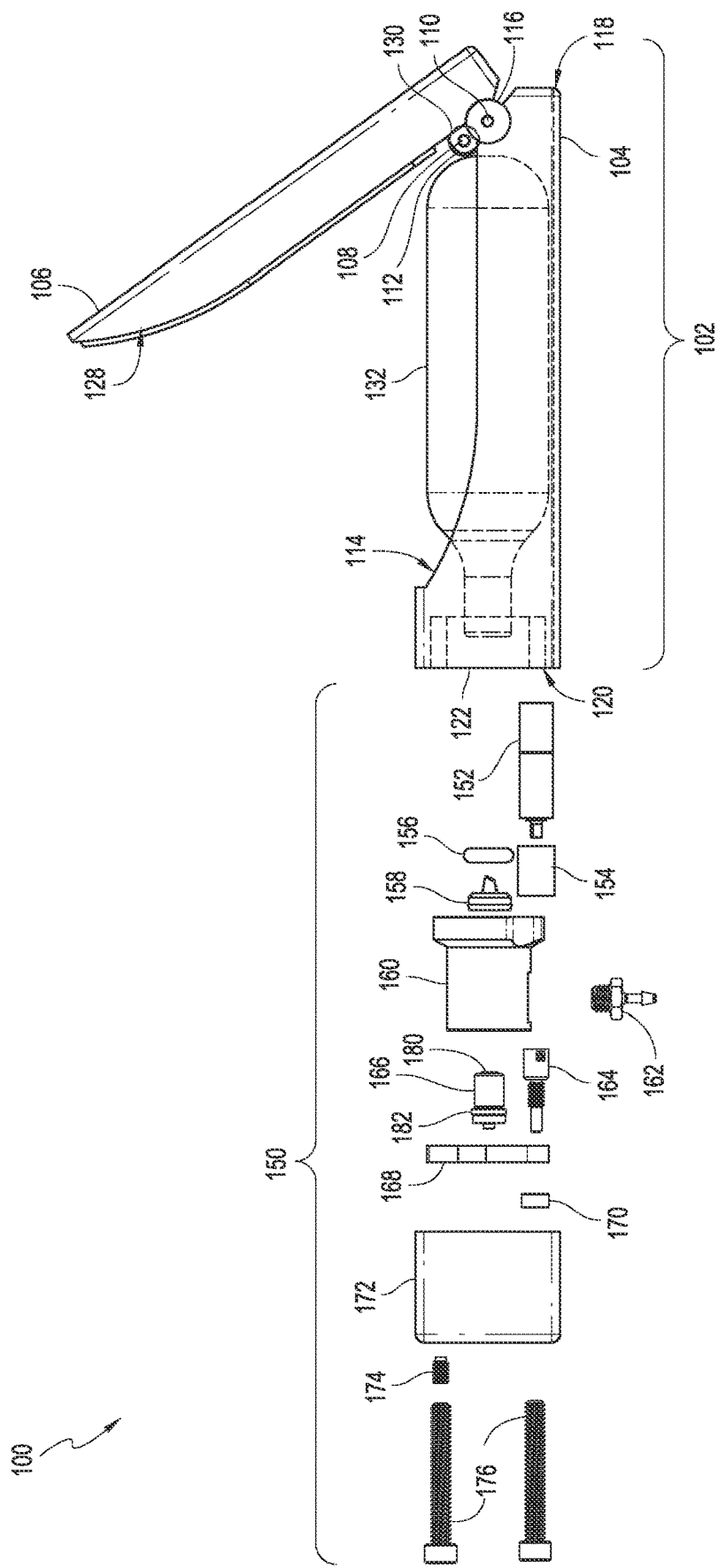
FIGS. 2-5 are exploded perspective views of an embodiment of a valve-chamber assembly.
Figure 3:
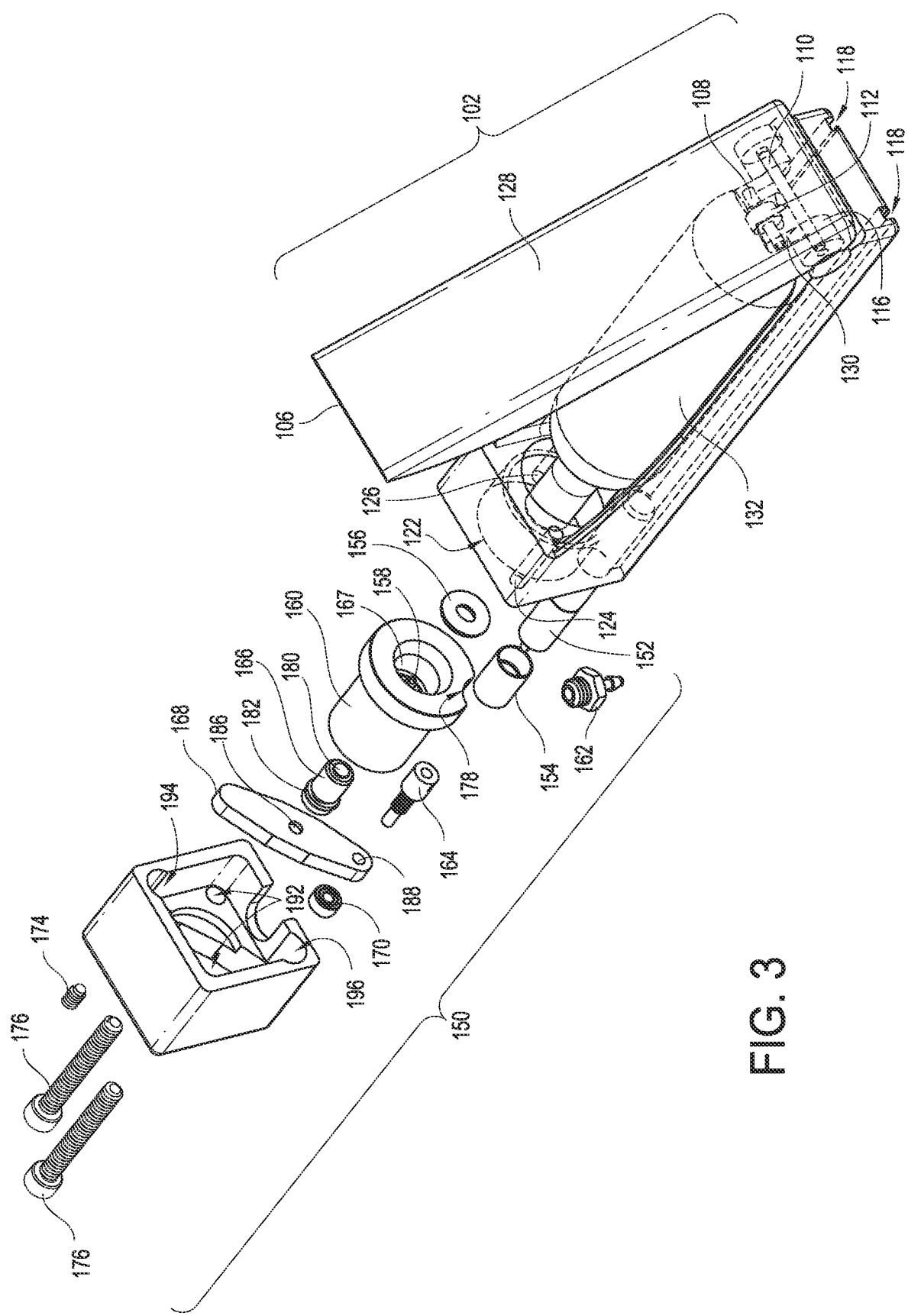
Figure 4:
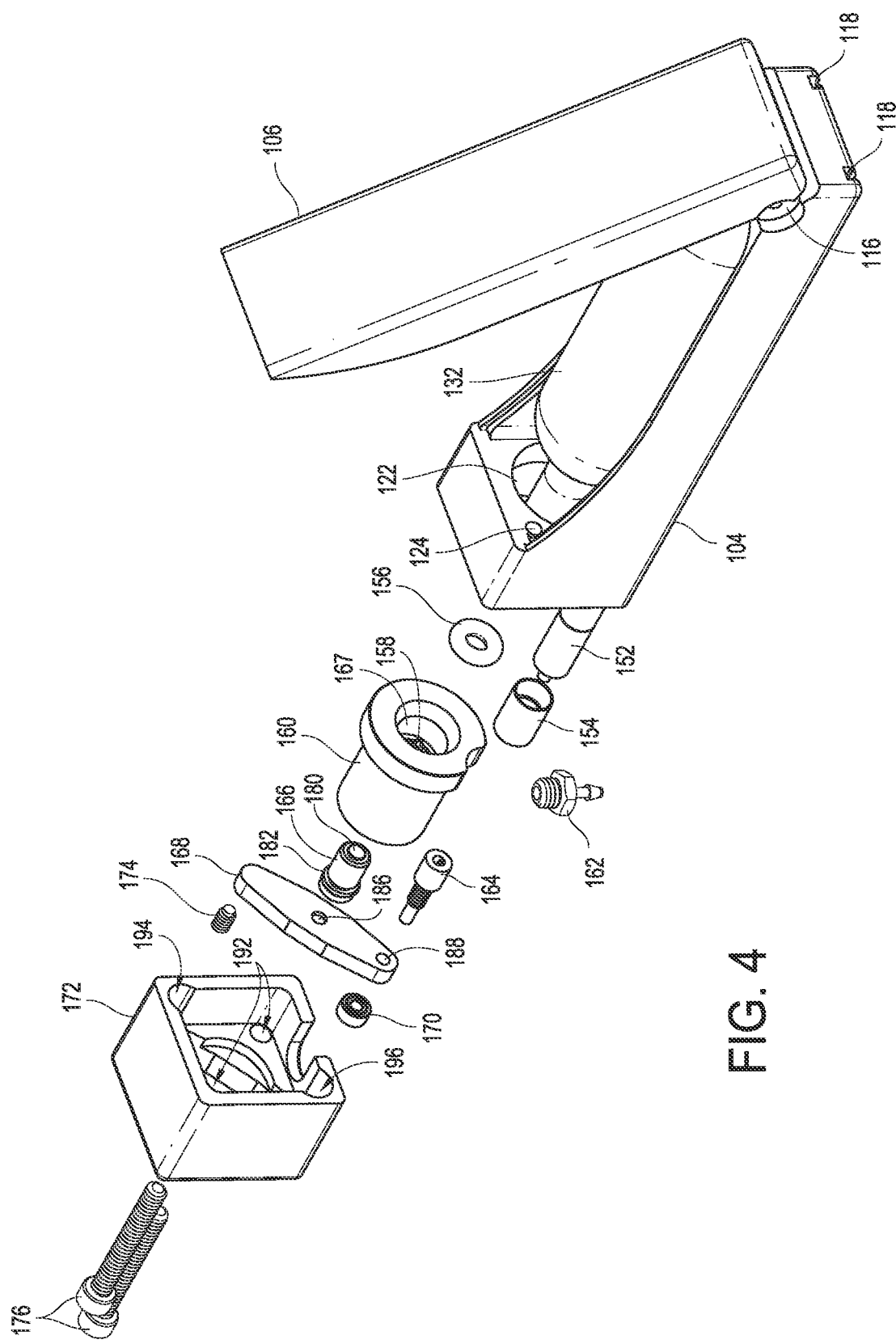
Figure 5:
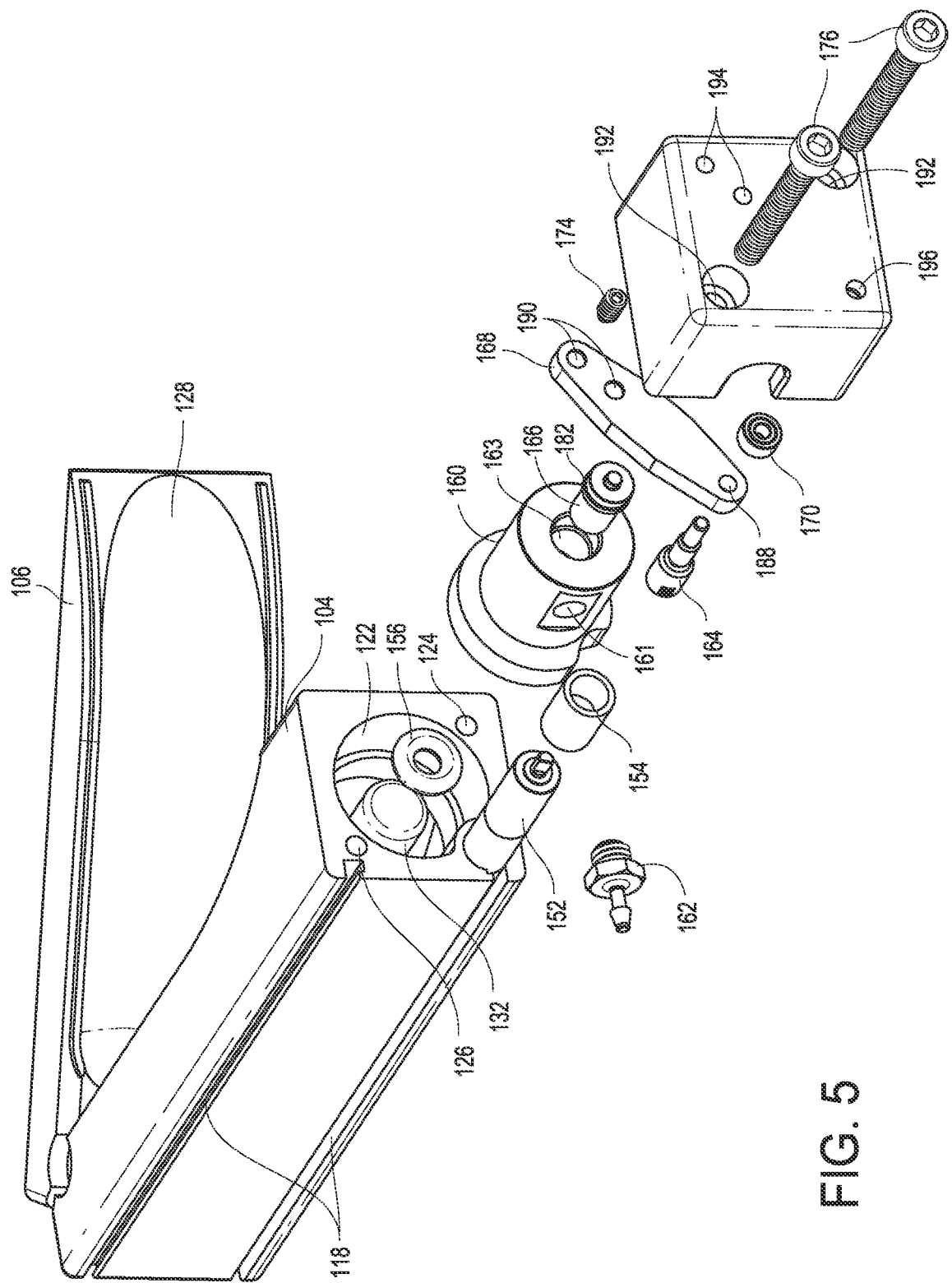
Figure 6:
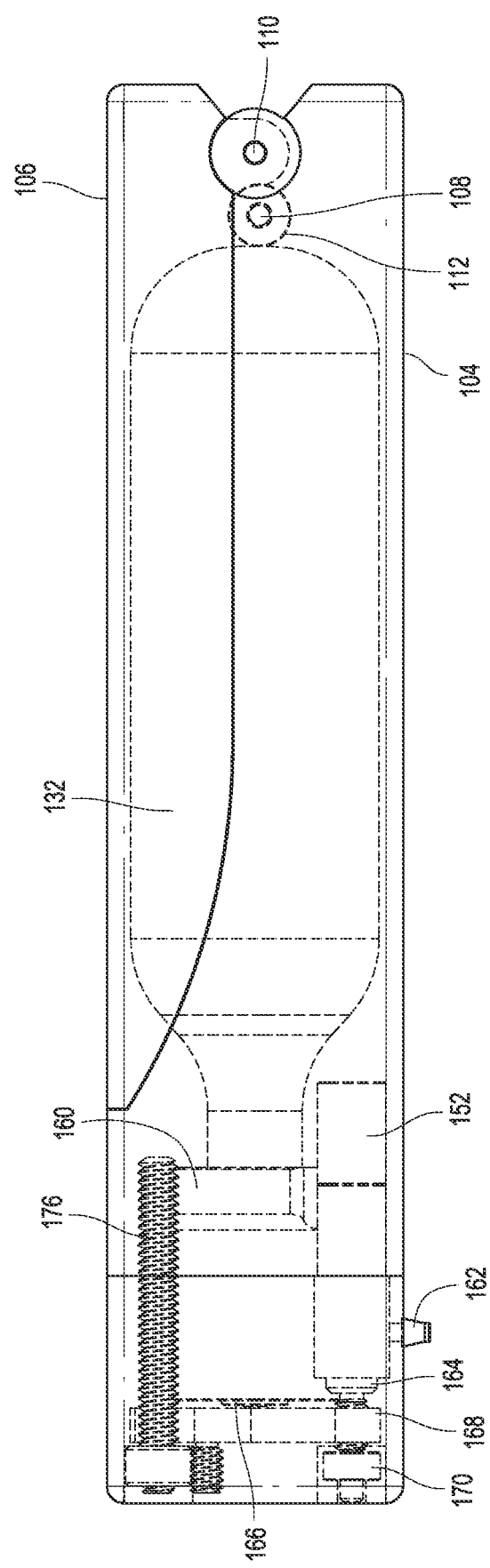
FIGS. 6 and 7 are perspective views of an embodiment of a valve-chamber assembly.
Figure 7:
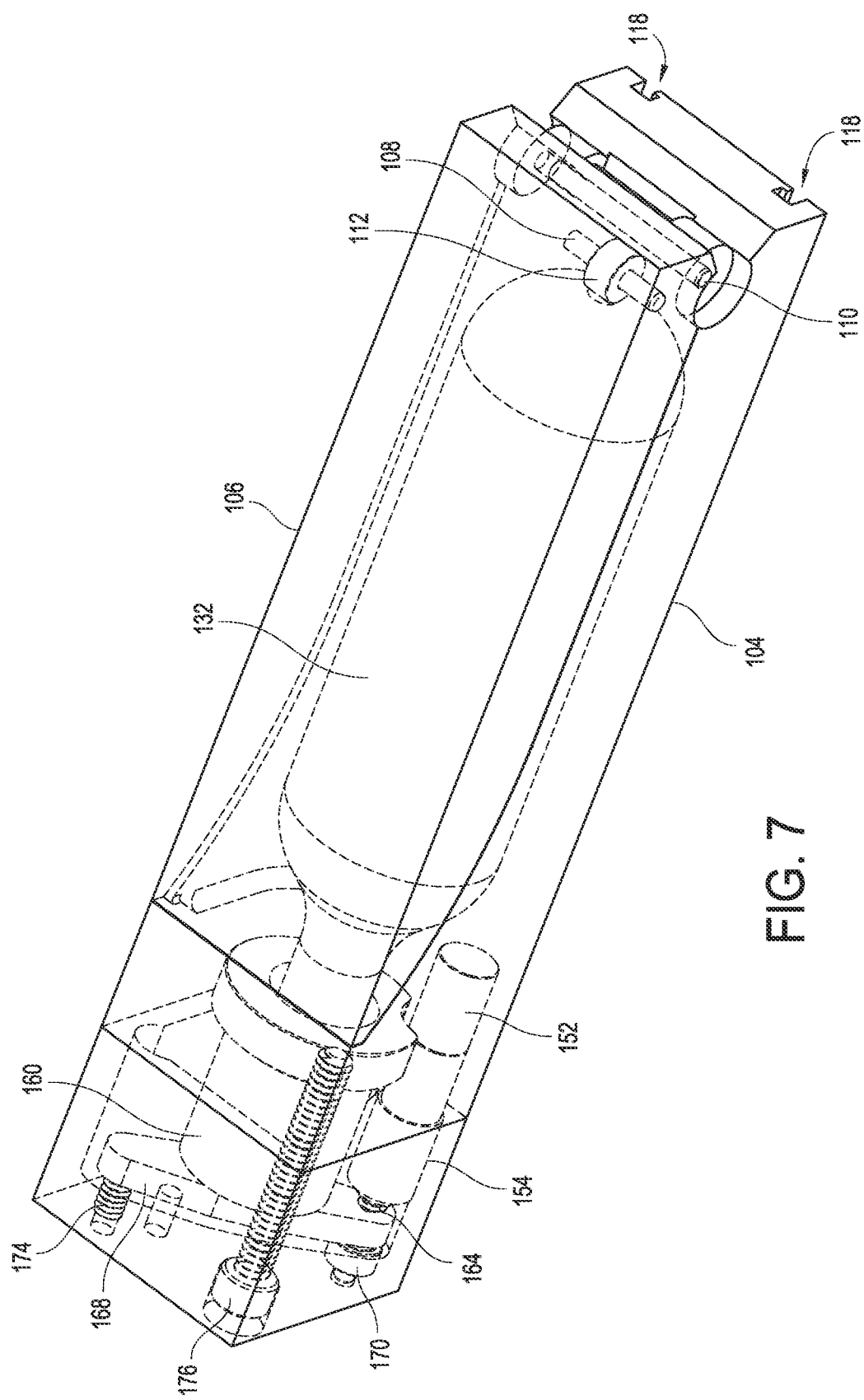

FIG. 1B is a drawing illustrating an embodiment of the blood pressure monitoring system 10 configured to be worn by a user. As discussed in greater detail above and shown in FIG. 1B, the blood pressure monitoring system 10 can include an inflatable cuff 20, a patient monitor 30, a valve-chamber assembly 100, and a gas reservoir 40 embodied as the gas canister 132. In the illustrated embodiment, the inflatable cuff 20 and chamber 306 can be removably attached to the patient monitor 30.

In addition, in the illustrated embodiment, the inflatable cuff 20 includes an arm band and can be wrapped around an arm of a user. The inflatable cuff 20 can include one or more attachment surfaces 326A, 326B to maintain the inflatable cuff 20 in a relatively fixed position around the arm of the user. In the illustrated embodiment, the attachment surfaces 326A, 326B are located on either side of the patient monitor 30. In some embodiments, the attachment surfaces 326A, 326B are located on one side of the patient monitor 30, or there is only one attachment surface. The attachment surfaces 326A, 326B can be made from a variety of different materials, such as, but not limited to, hook and loop type fasteners, buttons, snaps, hooks, latches, tape, or other device capable of maintaining the inflatable cuff 20 in a substantially fixed position about the user.

Although not illustrated in FIG. 1B, as described previously, the blood pressure monitoring system 10 can further include one or more sensors capable of detecting one or more physiological parameters of the user. The sensors can communicate with the patient monitor 30 via wired or wireless communication using a variety of protocols, including, but not limited to, TCP/IP, Bluetooth, ANT, ANT+, USB, Firewire, etc.

As described in greater detail above and illustrated in FIG. 1B, the patient monitor 30 can include the display 60, a communications link indicator 312 (implemented as either hardware or software to indicate whether a communication link is active and/or functioning), and user interface objects 314, 316. In some embodiments, the patient monitor 30 can further include a power monitor that determines the amount of power remaining for use by the patient monitor 30. When the patient monitor is battery-operated, the power monitor can determine the amount of time or the number of blood pressure measurements that remain before the batteries are to be replaced or recharged.

The patient monitor 30 can be a device dedicated to the measurement of physiological parameters or can be a portable electronic device configured to measure physiological parameters. In some embodiments, the patient monitor 30 is a portable electronic device, such as a smartphone, tablet, or the like, running a program or application configured to calculate physiological parameters based on signals received from the sensors.

As described in greater detail in the '225 application, the patient monitor 30 can receive data from one or more sensors and processes the data to extract physiological parameters of the user, and display on the display 60 physiological parameters, such as heart rate 318 and blood pressure data 320, 322. The patient monitor can also provide activity recommendations based on the physiological parameters of the user.

In some embodiments, the patient monitor 30 can also display a health indicator 324, which can indicate an overall well-being of a user. The health indicator 324 can be based on the heart rate data 318, blood pressure data 320, 322, other physiological parameters, or any combination thereof, and. For example, if the patient monitor 30 determines that the blood pressure data 320, 322 is normal, an arrow can point to the middle of the health indicator 324 or the health indicator 324 can be green, etc. If the patient monitor 30 determines that the blood pressure data 320, 322 is high or low, the arrow can point to the top or bottom health or the health indicator 324 can be red or blue, etc. Similarly, other physiological parameters or a combination of physiological parameters can be used by the health indicator 324.

The user interface objects 314, 316 can be implemented using hardware or software. For example, the user interface objects 314, 316 can be buttons or keys, form part of the display 60, or any combination thereof. The user interface objects 314, 316 can be used to interface with the patient monitor 30. For example, the user interface object 314 can be used to select one or more options from the patient monitor 30, such as which physiological parameters to display, how to display the physiological parameters, toggle between which sensors to use, view historical physiological parameter data, etc. In addition, the user interface objects 314, 316 can be used to determine the frequency with which blood pressure measurements should be taken. For example, using the user interface objects 314, 316 the patient monitor 30 can be configured to automatically take blood pressure measurements sequentially as determined by a user, or can be configured to take only one blood pressure measurement before requiring additional input from the user. For example, in some embodiments, by pushing or holding down a user interface object, the patient monitor 30 will automatically toggle between a single measurement mode and a sequential measurement mode. Furthermore, the user interface objects 316 can be used to scroll through one or more options displayed on the display 60. Other user interface objects can be used as desired.

Chamber Assembly

With reference to FIGS. 2-10, in some embodiments, the chamber assembly 102 can include a housing 104, a cover 106, pins 108, 110, a bearing 112, each of which can be made of metal, plastic, another rigid material, or any combination thereof. The pins 108, 110 and bearing 112 can create a hinged joint that couples the housing 104 to the cover 106. For example, the pin 108 can be placed through hollowed portions 116 of the chamber housing 104 and the chamber cover 106. The housing 104 and cover 106 can further interface via pin 110 and the bearing 112. The pin 110 can be placed through hollowed portions 130 of the cover 106 and a center of the bearing 112. In some embodiments, the pins 108, 110 can be arranged to form a geometric lock or other lock configuration. For example, the distance between the pin 108 and the side of the housing 104 that includes the tracks 118 can be less than the distance between the pin 110 and the side of the housing 104 that includes the tracks 118.

An inner surface 128 of the cover 106 can be grooved to form fit with a gas canister 132. Although illustrated as being rounded, the gas canister 132 can be a different shape, such as a prism, pyramid, bulbous, and the like. Furthermore, it will be understood that the inner surface 128 of the cover 106 can be any shape to interface with the gas canister 132. In addition, in some embodiments, multiple gas canisters can be placed within the chamber assembly. When multiple gas canisters are used, they can be placed next to each other (in parallel) in the housing 104 or one after another (serially). When placed serially, each gas canister can include two heads, and a valve can be inserted between a head of one gas canister and the head of another gas canister. In some embodiments the gas canister heads can include threaded portions that engage with threaded portions of the valve. In certain embodiments, the valve can include clamping mechanism that clamps around the head of the gas canisters. In addition, the valve can include a pointed portion on either side that can puncture the top of a lower gas canister and the bottom of an upper gas canister allowing the gas to flow between the canisters. In this manner, multiple gas canisters can be used together.

The inner surface 114 of the housing 104 can be grooved to form fit with the gas canister 132. In addition, the housing 104 can include a number of cavities 120, 124, 126 and openings 122 to interface with components of the valve assembly 150. In some embodiments, a portion of the housing 104 that is proximal the valve assembly 150 (e.g., the opening 122, or the exterior of the housing 104) can be threaded in order to engage with a complementary threaded valve assembly 150 (e.g., the interior or exterior of the valve 160 and/or valve 1460), as described in greater detail in the '225 application previously incorporated herein. In certain embodiments, the valve assembly 150 and the chamber assembly 102 can be pressed together or use some other mechanical locking mechanism to be coupled together. In addition, the housing 104 can also include one or more tracks 118 to couple with another device, such as an arm band, patient monitor, bicycle, etc. The one or more tracks 118 can be located in the center of the housing 104 or off-center. Furthermore, the one or more tracks 118 can be grooves that interface with corresponding protrusions from the other device, or vice versa.

When open, the cover 106 can provide space for a user to insert the gas canister 132 into the housing 104. Once closed, the cover 106 and/or bearing 112 can exert an upward force on the gas canister 132, which causes the gas canister 132 to be pushed into and engage the valve assembly 150. As will be described in greater detail below, the valve assembly 150 can include a piercing pin 158, pincher, or other sharpened or pointed object that can interface with the upper portion, or seal, of the gas canister 132, and break the seal of the gas canister when a sufficient force is exerted against the gas canister 132 from the bearing 112.

In some embodiments, by merely closing the cover 106, the gas canister 132 can be positioned such that the upper portion, or seal, of the gas canister 132 can be broken by the valve assembly 150. In certain embodiments, after closing the cover 106, a fastening assembly, which will be described in greater detail below with reference to FIGS. 13 and 14A-14D, can be used to position the gas canister such that the upper portion, or seal, of the gas canister 132 can be broken by the valve assembly 150.

Once broken, the gas from the gas canister 132 can move through the valve assembly 150 and a gas pathway to an end point, such as an inflatable blood pressure cuff, inflatable tire, inflatable tube, etc. For example, in some embodiments, the valve assembly 150 interfaces with a patient monitor and an inflatable cuff, as described in greater detail in the '225 application, previously incorporated herein.

In addition, when closed, the cover 106 can interact with the housing 104 so that the cover 106 remains closed. For example, a clasp, hook, magnet or locking assembly, as will be described in greater detail below with reference to FIG. 11, can couple the cover 106 with the housing 104 to prevent the cover 106 from opening during use, or while pressurized gas is present in the valve assembly 150 or gas canister 132.

Valve Assembly Embodiments

With continued reference to FIGS. 2-10, in some embodiments, the valve assembly 150 can include a motor 152, motor shield 154, pressure ring 156, piercing pin 158, valve 160, output nozzle (or output port) 162, actuator 164, piston 166, bar lever 168, bearing 170, valve cover 172, a set bolt 174, and securing bolts 176, each of which can be made of metal, plastic, rubber, elastomer, a rigid material, a composite material, or any combination thereof. However, it will be understood that the valve assembly can be implemented in a variety of ways, as described in greater detail below with reference to FIGS. 15A-15E.

The valve cover 172 can be used to protect the components of the valve assembly 150 from the elements, as well as aid in aligning the components with each other. The securing bolts 176 can be used to secure the valve cover 172 to the chamber assembly 102 via the holes 192 of the valve cover and the cavities 126, 124 of the housing 104. When assembled, the components of the valve assembly 150 can be found between the valve cover 172 and the housing 104.

The valve 160 can include a low pressure cavity 163 that is distally located from the chamber assembly 102, a high pressure cavity 167 that is proximally located from the chamber assembly 102, and a high/low pressure channel 165 (FIGS. 8 and 9) that provides a gas pathway between the two cavities 163, 167. The valve 160 can further include an output channel 161 that engages with the output nozzle 162. The output nozzle 162 can be hollow to allow gas to flow through it to an end point. The valve 160 can also include a groove 178. The groove 178 can help align the valve 160 with the motor 152 and can further enable a more compact valve assembly 150.

The piercing pin 158 and the pressure ring 156 (e.g., an O-ring) can be located within the high pressure cavity 167 of the valve 160 and interface with the seal of the gas canister 132. The piercing pin 158 can be hollow and relatively pointed or sharp. Accordingly, the piercing pin 158 can be used to break the seal of the gas canister 132. The pressure ring 156 can form a seal around the nozzle of the gas canister 132, and prevent gas leakage from the high pressure cavity 167 of the valve 160.

The piston 166 can be located in the low pressure cavity 163 of the valve 160. A bushing 180 and an O-ring 182 can be coupled to the piston 166 to prevent gas leakage. A protrusion 184 on the upper portion of the piston 166 can engage with an indention 186 found on the side of the bar lever 168 that is proximal to the chamber assembly 102. Once a preferred initial position of the bar lever 168 is determined and the valve cover 172 positioned, the set bolt 174 can be screwed into a hole 194 and used to maintain the bar lever 168 in the initial position until moved by the actuator 164, as will be described below. For example, the set bolt 174 can be screwed into the hole 194 until a threshold torque is reached. The torque threshold can be based on an expected force resulting from the pressurized gas exiting the gas canister 132.

When the seal of the gas canister 132 is broken, the pressurized gas enters the high pressure cavity 167, passes through the center of the pressure ring 156, the cavity in the piercing pin 158, the channel 165, and exerts an upward force against the piston 166. The upward force on the piston 166 is in turn transferred to the bar lever 168. However, as long as the downward force exerted on the bar lever 168 from the set bolt 174, the valve cover 172, and/or the actuator 164 is greater than the force of the piston 166, the bar lever 168 will remain stationary and the piston 166 will remain in place.

The motor 152 can be a gear motor or other electric motor, and can be used to open and close a gas pathway between the high pressure cavity 167 and the output channel 161. In some embodiments the gear motor can cause an end thereof to rotate in a clockwise or counter-clockwise fashion. In certain embodiments, the motor 152 can cause the end thereof to extend or retract.

A portion of the motor 152 that is proximal to the chamber assembly 102 can engage with the housing 104, such as within a cavity 120 of the housing 104. In some embodiments, the motor 152 is affixed within the cavity 120, such as by form-fitting, molding, gluing, etc. The portion of the motor 152 that is distal to the chamber assembly 102 can be covered with the motor shield 154 to reduce movement of the motor within the cavity 120.

Furthermore, in some embodiments, the end of the motor 152 can engage with a portion of the actuator 164 that is proximal to the chamber assembly 102. In some embodiments, when the motor 152 actuates, the actuator 164 can rotate in a clockwise or counter-clockwise fashion to open or close the gas pathway between the high pressure cavity 167 and the output channel 161. In certain embodiments, when the motor 152 actuates, the actuator 164 can extend towards, or retract from, the bar lever 168 to open or close the gas pathway between the high pressure cavity 167 and the output channel 161. An end of the actuator 164 can engage a bearing 170 placed within a hole 196 of the valve cover 172. The bearing 170 can act as a buffer between the actuator 164 and the valve cover 172 to prevent damage.

Although described as being located in the cavity 120, it will be understood that the motor 152 can be placed in a variety of locations. For example, the valve cover 172 can include a cavity similar to the cavity 120 of the illustrated embodiments. In such embodiments, a portion of the motor 152 can be located within the cavity in the valve cover and the portion of the motor that engages with the actuator 164 can be proximally located to the chamber assembly 102.

In some embodiments, the actuator 164 can include threads that engage complementary threads in a hole 188 of the bar lever 168 such that rotational movement of the actuator 164 causes the actuator 164 to advance through the hole 188 in one direction or another. As the actuator 164 advances through the hole 188 it can exert a force on the bar lever 168 causing the bar lever 168 to move in substantially the same direction as the trajectory of the actuator 164. In some embodiments, when the actuator 164 rotates in a first direction, it exerts an upward force on the bar lever 168, and can create or open the gas pathway between the high pressure cavity 167 and the output channel 161. When the actuator 164 rotates in a second direction that is substantially opposite the first direction, it can reduce the amount of upward force on the bar lever 168, exerts a downward force on the bar lever 168, or exerts no force on the bar lever 168, and can close, seal, or remove the gas pathway between the high pressure cavity 167 and the output channel 161.

In certain embodiments, the actuator 164 extends towards, or retracts from, the bar lever 168 to open or close the gas pathway between the high pressure cavity 167 and the output channel 161. In such embodiments, when the actuator extends towards the bar lever 168, it can exert an upward force against the bar lever 168. When the actuator retracts from the bar lever it can reduce the amount of upward force on the bar lever 168, exert a downward force on the bar lever 168, or exert no force on the bar lever 168. In embodiments where the motor 152 is located distally from the chamber assembly 102 with respect to the bar lever 168, the force exerted by the actuator 164 when extended or retracted can be reversed.

It will be understood that the actuator 164 and the bar lever 168 can interface using different mechanisms as well. For example, in some embodiments, the actuator 164 can be used to push the bar lever 168 in one direction and/or to pull the bar lever 168 in a substantially opposite direction, push but not pull actuator 164, and/or pull but not push the actuator 164. In some embodiments, once the bar lever 168 is displaced by the actuator 164, the valve assembly 150 can rely upon other forces acting on the bar lever 168 (e.g., gravity, set bolt 174, valve cover 172, etc.) to return it to its initial position.

Figure 8:
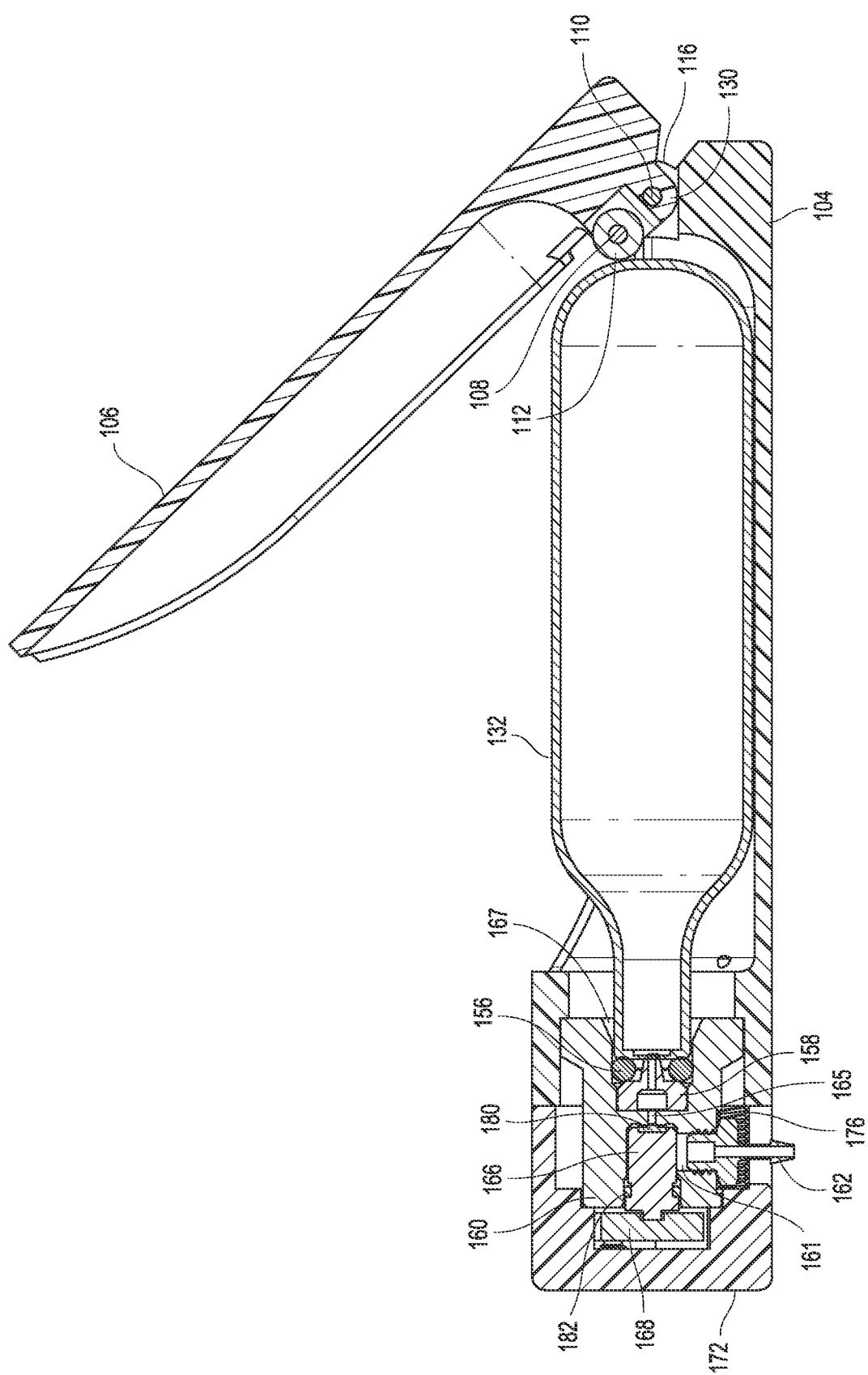
FIGS. 8-10 are cross-sectional views of an embodiment of a valve-chamber assembly.
Figure 9:
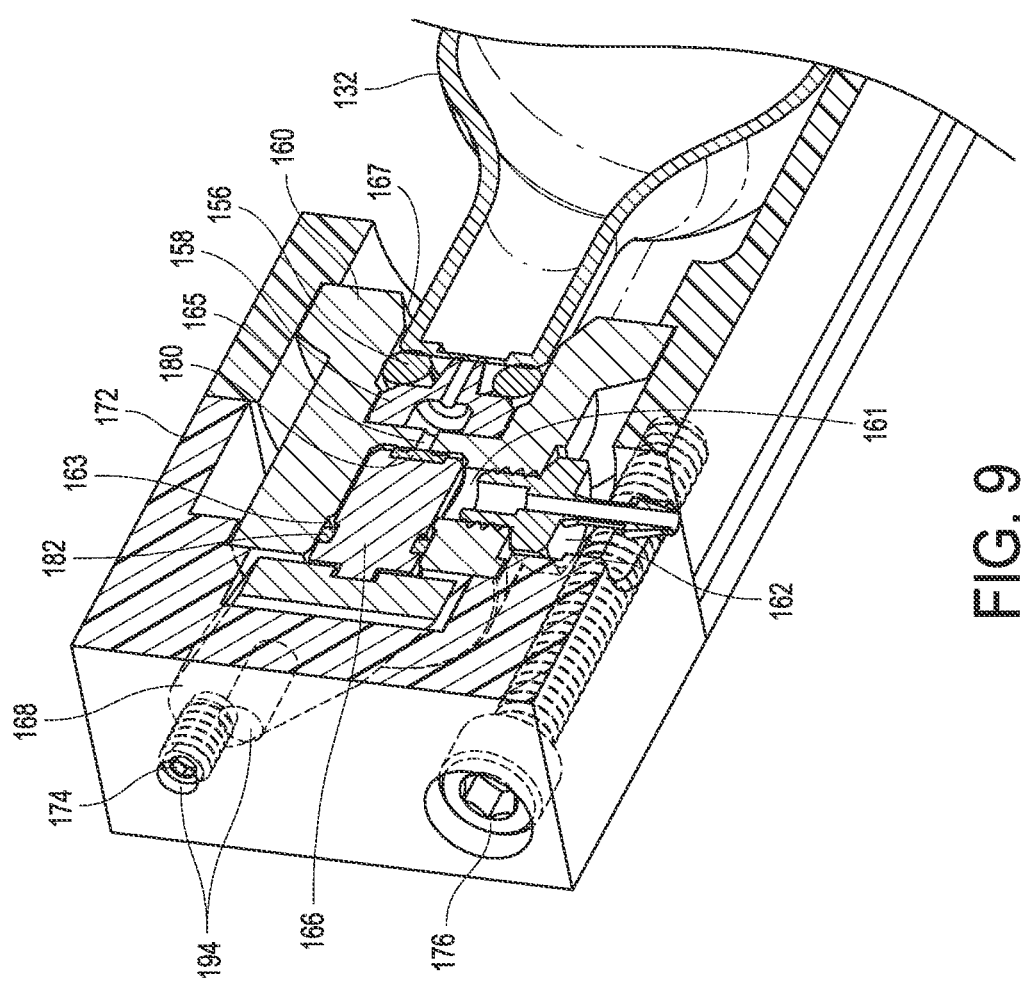
Figure 10:
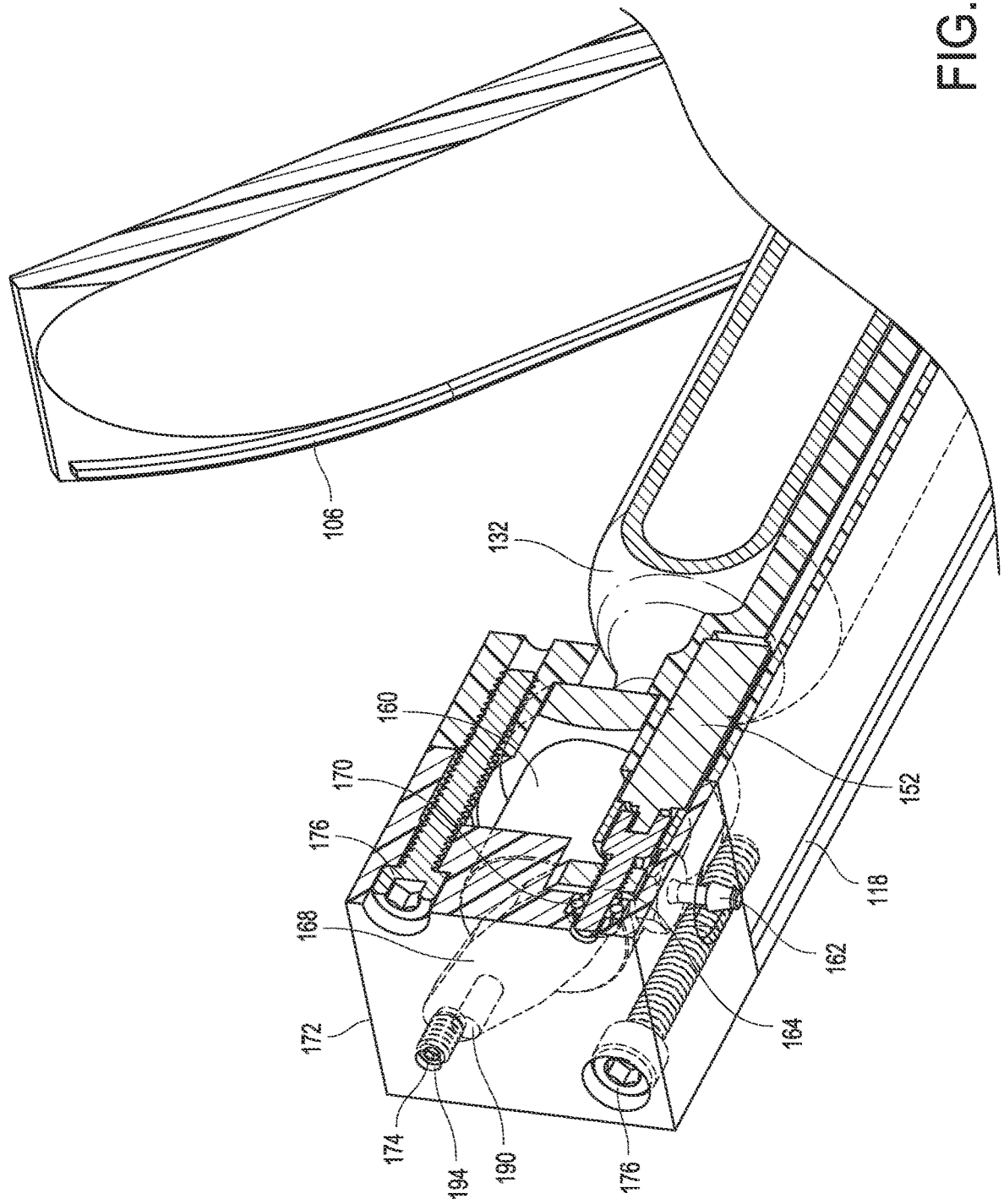

An embodiment of the operation of the valve-chamber assembly 100 will now be described with reference to FIGS. 8-10, which are cross-sectional views of an embodiment of the valve-chamber assembly 100.

As described previously, closing the chamber cover 106 causes the bearing 112 to exert an upward force on the gas canister 132. The upward force on the gas canister 132 causes the gas canister 132 to engage with the pressure ring 156 and the piercing pin 158. The piercing pin 158 breaks the seal of the gas canister 132, thereby releasing the gas from the gas canister 132. The gas flows through the hollowed portion of the piercing pin 158 and into the high/low pressure channel 165 of the valve 160. The pressure from the gas causes an upward force to be exerted against the piston 166. However, so long as the downward force exerted on the piston 166 by the bar lever 168 and/or valve cover 172 is equal to or greater than the force exerted by the gas, the piston 166 remains stationary and the gas remains enclosed within the valve high/low pressure channel 165 and/or the low pressure cavity 163.

The motor 152 and actuator 164 can be used to create a gas pathway between the high/low pressure channel 165 and the output channel 161, thereby enabling gas to flow from the high/low pressure channel 165 to the output channel 161, and out the output nozzle 162. As described previously, actuating the motor 152 can cause the actuator 164 to exert an upward force on the bar lever 168. The upward force exerted by the actuator 164 on the bar lever 168 reduces the downward force exerted by the bar lever 168 against the piston 166. In some embodiments, the upward force exerted by the actuator 164 causes the bar lever 168 to move, creating a space between the bar lever 168 and the piston 166.

Once the downward force exerted by the bar lever 168 on the piston 166 is less than the upward force exerted by the pressurized gas (or if the bar lever 168 has moved distally away from the chamber assembly 102), the piston 166 moves distally away from the chamber assembly 102 and the valve high/low pressure channel 165 due to the upward force exerted from the pressurized gas in the channel 165. The movement of the piston 166 distally from the high/low pressure channel 165 can create a gas pathway in the low pressure cavity 163 from the high/low pressure channel 165 to the output channel 161, and allow the gas to travel from the high/low pressure channel 165 to the output channel 161, and to the output channel 161. Once in the output channel 161, the gas can flow through the output nozzle 162.

The motor 152 and the actuator 164 can likewise be used to seal the output channel 161 from the valve high/low pressure channel 165 and to close the gas pathway. Reversing the polarity of the motor 152 can cause the actuator 164 to advance in the opposite direction. The movement of the actuator 164 in the opposite direction reduces the upward force exerted on the bar lever 168 and, in some embodiments, can create a downward force on the bar lever 168. Once the total upward force exerted by the actuator 164 and/or the piston 166 on the bar lever 168 is less than the downward force exerted on the bar lever 168 by the set bolt 174, valve cover 172, and/or actuator 164, the piston 166 moves proximally towards the chamber assembly 102 and the gas pathway between the valve high/low pressure channel 165 and the output channel 161 closes.

The flow rate of the gas can also be controlled by actuating the motor 152 to vary the distance between the piston 166 and the channel 165. An increased distance between the piston 166 can result in a higher flow rate and a decreased distance can result in a lower flow rate. In some embodiments, a pressure sensor at the endpoint, such as a pressure sensor on a blood pressure cuff, or along a gas pathway to the endpoint, monitors the change in pressure due to the flow of gas. The change in pressure monitored by the pressure sensor can be used to control the actuation of the motor. For example, the rate at which pressure is increasing can be compared to a preferred rate. If the measured rate is less than the preferred rate, or less than a determined variance from the preferred rate, the motor 152 can increase the flow rate. In some embodiments, the motor 152 can increase the flow rate by increasing the upward force exerted against the bar lever 168 and/or moving the bar lever distally from the chamber assembly 102. Likewise, if the measured rate is greater than the preferred rate, or greater than a determined variance from the preferred rate, the motor can decrease the flow rate. In certain embodiments, to decrease the flow rate, the motor 152 can decrease the upward force exerted against the bar lever. In addition, once a determined pressure level is achieved, the motor 152 can close the gas pathway.

Lock Assembly

Figure 11:
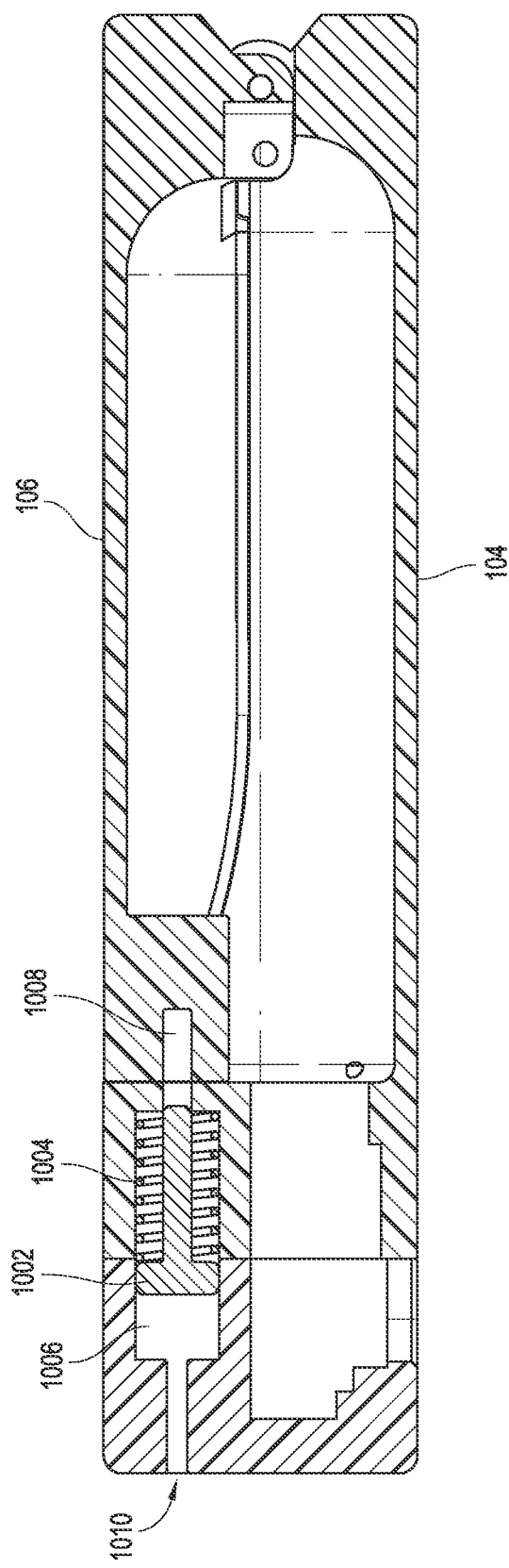
FIG. 11 is a diagram of an embodiment of a lock assembly of the valve-chamber assembly.

FIG. 11 is a diagram of an embodiment of a lock assembly 1000 for the valve-chamber assembly 100. Advantageously, the lock assembly 1000 can provide a safety mechanism to prevent a user from opening the chamber assembly 102 when pressurized gas from the gas canister 132 is present in the valve assembly 150. The lock assembly 1000 can include a pin 1002 and a spring 1004 located in a pin cavity 1006 of the housing 104. In some embodiments, the lock assembly 1000 can further include one or more pressure seals located on either side of the pin 1002 to prevent gas leakage.

The housing 104 can include a gas channel 1010 extending from the valve 160 to the pin cavity 1006. For example, the gas channel 1010 can extend from the high pressure cavity 167, the low pressure cavity 163, and/or the high/low pressure channel 165 to the pin cavity 1006. The cover 106 can include a receiver cavity 1008.

The pin 1002 can include a head and an elongated portion. The spring 1004 can encircle at least a portion of the elongated portion of the pin 1002, and exert an upward force against the pin 1002 such that the pin 1002 remains within the pin cavity 1006 of the housing 104. Once the seal of the gas canister 132 is broken, the gas can flow from the valve 160 to the pin cavity 1006 through the gas channel 1010. The pressure from the gas can exert a downward force on the pin 1002. The spring 1004 can be selected such that the expected downward force on the pin 1002 from the pressurized gas exceeds the upward force on the pin 1002 from the spring 1004. In this way, the downward force from the pressurized gas causes the pin 1002 to move proximally towards the cover 106 and engage the receiver cavity 1008. Once the pin 1002 is engaged with the receiver cavity 1008, a user can be prevented from opening the cover 106. Once the gas canister 132 is empty or the valve 160 no longer contains pressurized gas sufficient to overcome the upward force of the spring 1004, the pin 1002 moves distally from the receiver cavity 1008 and returns to the pin cavity 1006, thereby unlocking the cover 106.

Valve Protection Circuit

Figure 12:
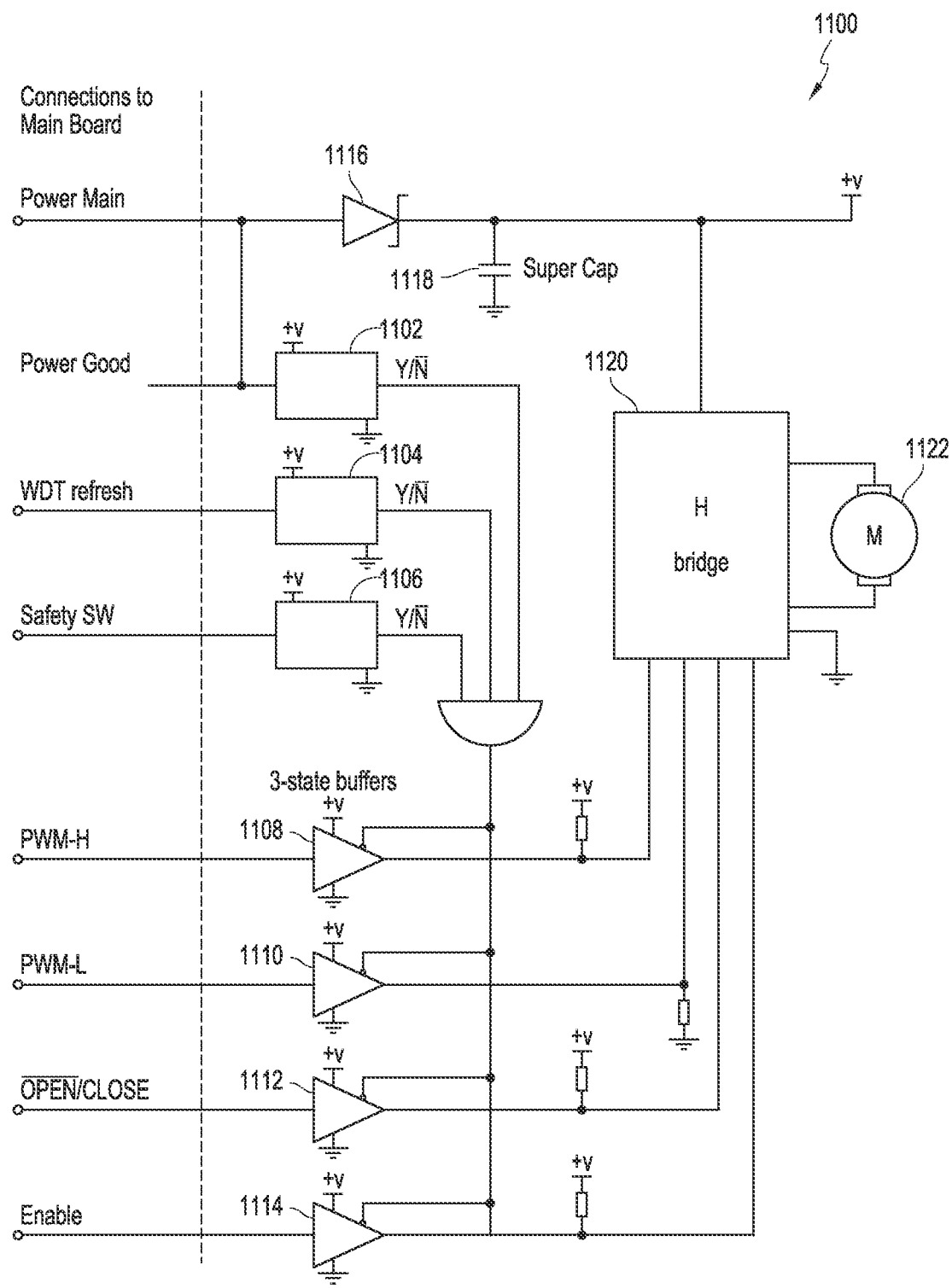
FIG. 12 is a diagram of an embodiment of a safety circuit for the valve-chamber assembly.

FIG. 12 is a block diagram of an embodiment of a valve protection circuit 1100. Advantageously, the valve protection circuit 1100 can be used to cut off gas flow from the gas canister 132 when a safety issue arises, or when a monitored safety parameter satisfies a threshold safety status, such as a loss of power, an alarm indicating pressure at an end point is too high or other alarm, a missing refresh signal from a controller, etc. In some embodiments, the valve protection circuit 1100 can be used to move the bar lever 168 (and piston 166) proximally towards the chamber assembly 102, thereby closing the gas pathway between the high/low pressure channel 165 and the output channel 161.

In the illustrated embodiment, the valve protection circuit 1100 includes one or more registers 1102, 1104, 1106; buffers 1108, 1110, 1112, 1114; a buffer 1116; a super capacitor 1118; and an H-bridge 1120 in communication with a motor 1122, such as the motor 152 described previously. The super capacitor 1118 can charge and remain charged when power is present. When power is not present, or when the control signals are communicatively disconnected from the H-bridge 1120, the super capacitor 1118 can discharge to the H-bridge 1120.

The registers 1102, 1104, and 1106 can be implemented using memory, such as RAM, flip-flops, latches, etc., and can be used to monitor different aspects, or safety control parameters, of the control system. As mentioned previously, the safety control parameters can include, but are not limited to, electrical power, pressure at an end point, a refresh signal from a controller, software alerts, etc. For example, the register 1102 can monitor whether sufficient electrical power is present, the register 1104 can monitor whether a refresh is received from a controller (e.g., microprocessor, microcontroller, field-programmable gate array (FPGA), programmable logic device, etc.), and the register 1106 can monitor whether a software safety signal is activated (e.g., software error, pressure at an endpoint exceeds a pressure threshold, etc.), It will be understood that other safety control parameters can be monitored as well.

The buffers 1108, 1110, 1112, 1114 can be implemented using tri-state buffers and used to regulate communication pathways between the control system and the H-bridge 1120, and the flow of control data to the motor 1122. For example buffers 1108 and 1110 can be used to regulate communication pathways between the high/low pulse-width modulation signals and the H-bridge 1120. Similarly, the buffer 1112 can be used to regulate a communication pathway between the control signal that causes the motor 1122 to open or close the gas pathway and the H-bridge 1120. The buffer 1114 can be used to regulate the communication pathway between the enable signal and the H-bridge 1120, or motor 1122.

During operation, if any monitored safety parameters satisfy a threshold status, the H-bridge 1120 can be communicatively disconnected from the control signals. For example, if any of the registers 1102, 1104, 1106 indicate that there is insufficient power, a refresh is not received, or there is a software safety issue (e.g., pressure at an end point exceeds a threshold pressure level), the buffers 1108, 1110, 1112, 1114, can move to a high impedance state. Once the buffers 1108, 1110, 1112, 1114, are in the high impedance state, the H-bridge 1120 can be communicatively disconnected from the control signals.

In addition, when any monitored safety parameters satisfy a threshold status, the super capacitor 1118 can discharge to the H-bridge 1120. The H-bridge 1120 can be configured such that when the super capacitor 1118 discharges, the H-bridge 1120 causes the motor 1122 and (and corresponding actuator) to move in a particular way. For example, the H-bridge can be configured such that the discharging super capacitor 1118 causes the motor to move the bar lever 168 (and piston 166) proximally towards the chamber assembly 102, thereby closing the gas pathway between the high/low pressure channel 165 and the output channel 161. In this manner, if power is lost, a refresh signal is not received properly, or a software safety warning is activated, the valve assembly 150 can cut off the flow of the gas from the gas canister 132.

Fastening Assembly

In some embodiments, the chamber assembly 102 can include a fastening assembly 1200, which can be used to engage the gas canister 132 with the valve assembly 150. The fastening assembly 1200 can be located at a portion of the chamber assembly 102 that is distal to the valve assembly 150, and in some embodiments can form part of the chamber assembly 102 (e.g., the base 1204 can form part of the housing 104 that is distal to the valve assembly 150). In certain embodiments, the fastening assembly 1200 is coupled to the chamber assembly 102 (e.g., using threaded portions of the chamber assembly 102 and the fastening assembly 1200, clamps, clasps, soldering, screws, etc.).

Figure 13:
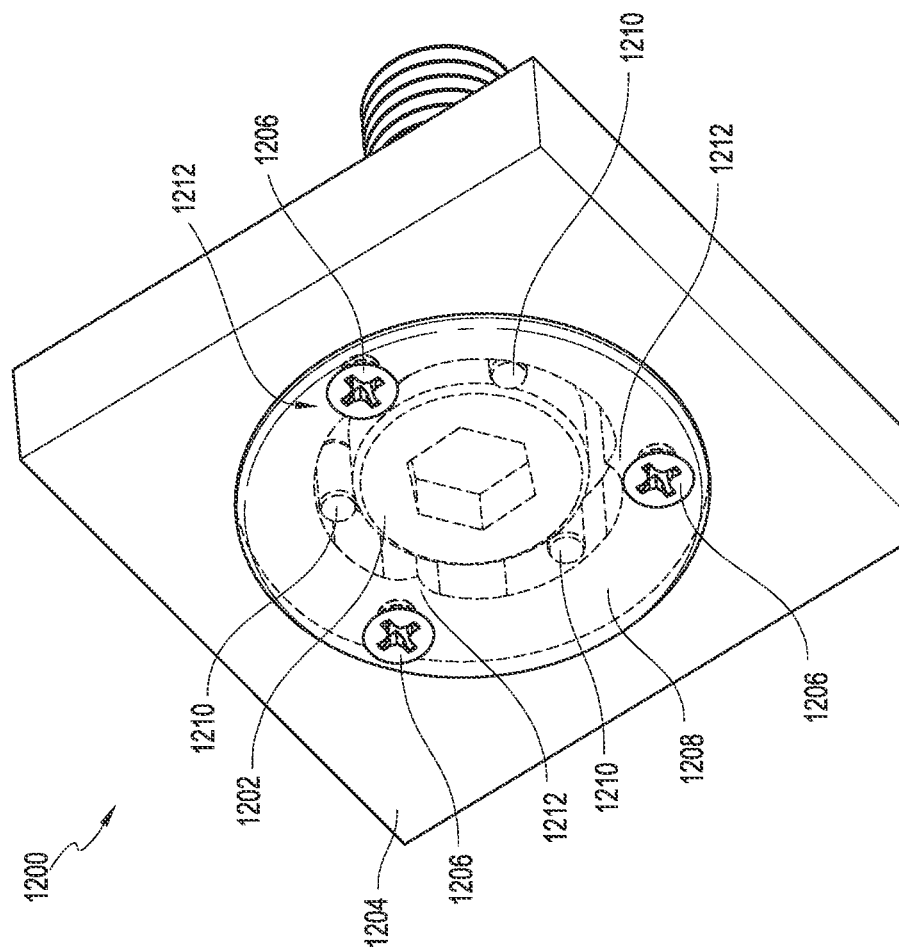
FIG. 13 is a diagram illustrative of an embodiment of a fastening assembly.

In the illustrated embodiment of FIG. 13, the fastening assembly 1200 includes a fastening bolt 1202, a base 1204, screws 1206, a locking ring 1208, and pillars 1210, each of which can be made of metal, plastic, rubber, an elastomer, a rigid material, a composite material, or any combination thereof. However, as will be discussed in greater detail below with reference to FIGS. 14A-14D, the fastening assembly 1200 can be implemented in a variety of ways.

The fastening bolt 1202 can be used to increase or decrease the upward force on the gas canister 132. For example, twisting, or rotating, the bolt 1202 in a clockwise or counter-clockwise direction can cause the fastening bolt (or screw) 1202 to move upward or downward, depending on the configuration of the bolt 1202. As the fastening bolt 1202 advances upward it can exert an upward force against the gas canister 132. The upward force can cause the seal of the gas canister 132 to move toward and engage with the piercing pin 158, causing the seal to break and release pressurized gas.

The base 1204, locking ring 1208 and pillars 1210 can be used to rotate the bolt 1202, and can interact in at least two distinct modes. The first mode can be used to position the base 1204 with respect to the rest of the chamber assembly 102, and the second mode can be used to engage the bolt 1202 with the gas canister 132.

In the first mode, the base 1204 and the locking ring 1208 can rotate about the pillars 1210 (or the base 1204 and pillars 1210 can rotate around the locking ring 1208 depending on the configuration). For example, in this mode, twisting the base 1204 (and locking ring 1208) does not cause the bolt 1202 to move upward or downward. Accordingly, the first mode can be used to position the base 1204 with the rest of the chamber assembly 102 after the gas canister 132 has engaged with the piercing pin 158. For example, after the gas canister 132 has engaged with the piercing pin 158, the edges of the base 1204 may not line up with the edges of the rest of the chamber assembly 102. By using the first mode, the base 1204 and chamber assembly 102 can be properly aligned.

The amount of movement permitted in the first mode can be based at least in part on the number of pillars 1210, the spacing between the pillars 1210, the number of protrusions 1212 of the locking ring 1208, and/or the spacing of the protrusions 1212. For example, in the illustrated embodiment, there are three equally-spaced pillars 1210 and three equally-spaced protrusions 1212 (two of which are visible in FIG. 13), and the base 1204 can rotate freely about the bolt 1202 for approximately 120°, at which point the pillars 1210 engage with the protrusions 1212. However, with four equally-spaced pillars 1210 and four equally-spaced protrusions 1212, the base 1204 can be configured to rotate freely about the bolt for approximately 90°. Similarly, with equally-spaced two pillars 1210 and two equally-spaced protrusions, the base 1204 can be configured to rotate freely about the bolt for approximately 180°, etc. Accordingly, the amount of movement permitted in the first mode can be configured as desired.

In the second mode, the base 1204 can be positioned such that the pillars 1210 engage with the protrusions 1212 of the locking ring 1208. In the second mode, rotating the base 1204 causes the bolt 1202 to rotate in a desired direction (e.g., in the same or opposite direction as the base 1204). When in the second mode, the bolt 1202 can be advanced upward or downward as desired. In some embodiments, the fastening assembly 1200 can be implemented with a single mode, such as the second mode. In such an embodiment, rotating the base 1204 can cause the bolt 1202 to move upward or downward, as desired.

FIGS. 14A-14D are diagrams illustrative of another embodiment of the fastening assembly 1200. In some embodiments, the fastening assembly 1200 includes a fastening bolt 1302 and a base 1304, each of which can be made of metal, plastic, rubber, an elastomer, a rigid material, a composite material, or any combination thereof. As described previously, the base 1304 can be rotated in a clockwise/counter-clockwise direction to cause the fastening bolt 1302 to advance upward or downward toward or away from the gas canister 132.

In some embodiments, the fastening assembly 1200 can also include a cover 1316 enclosing additional components of the fastening assembly 1200, and a latch 1310, which can reduce the amount of force required by a user to rotate the fastening bolt 1302. The latch 1310 and the cover can be made of metal, plastic, rubber, an elastomer, a rigid material, a composite material, or any combination thereof.

Figure 14A:
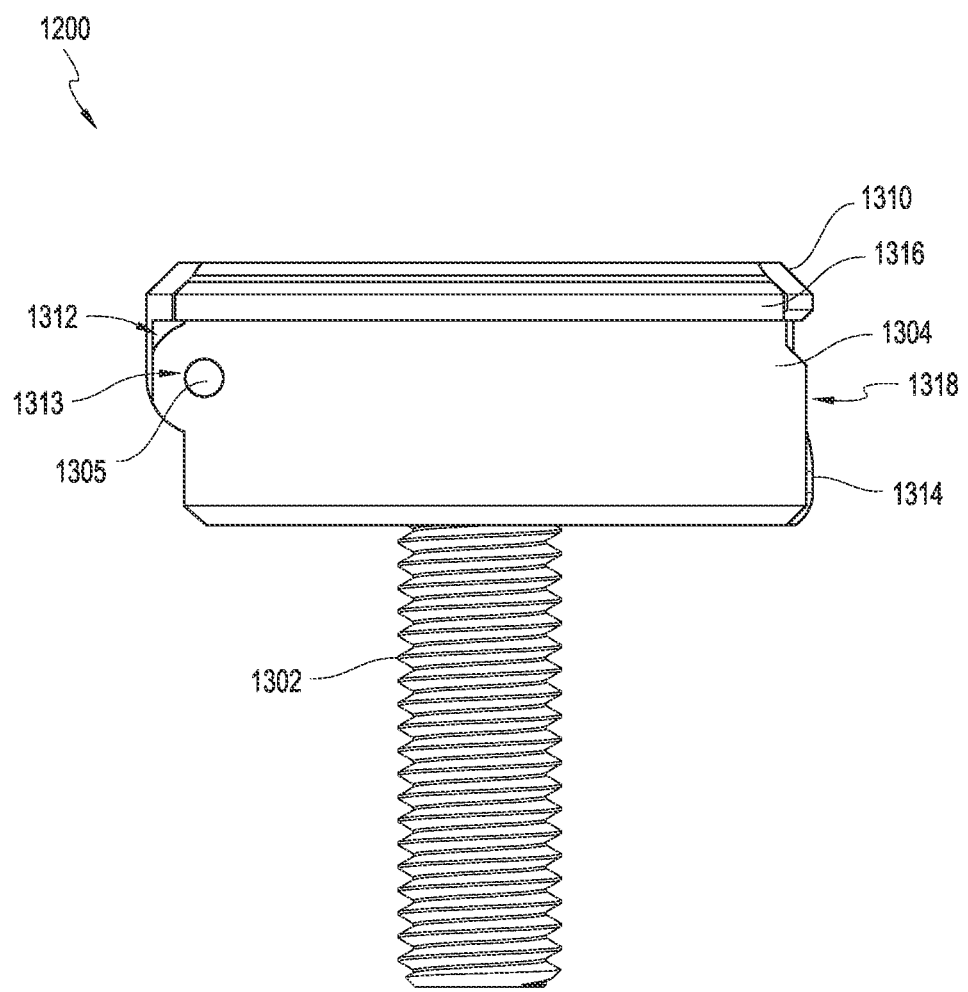
FIGS. 14A-14D are diagrams illustrative of an embodiment of a fastening assembly.
Figure 14B:
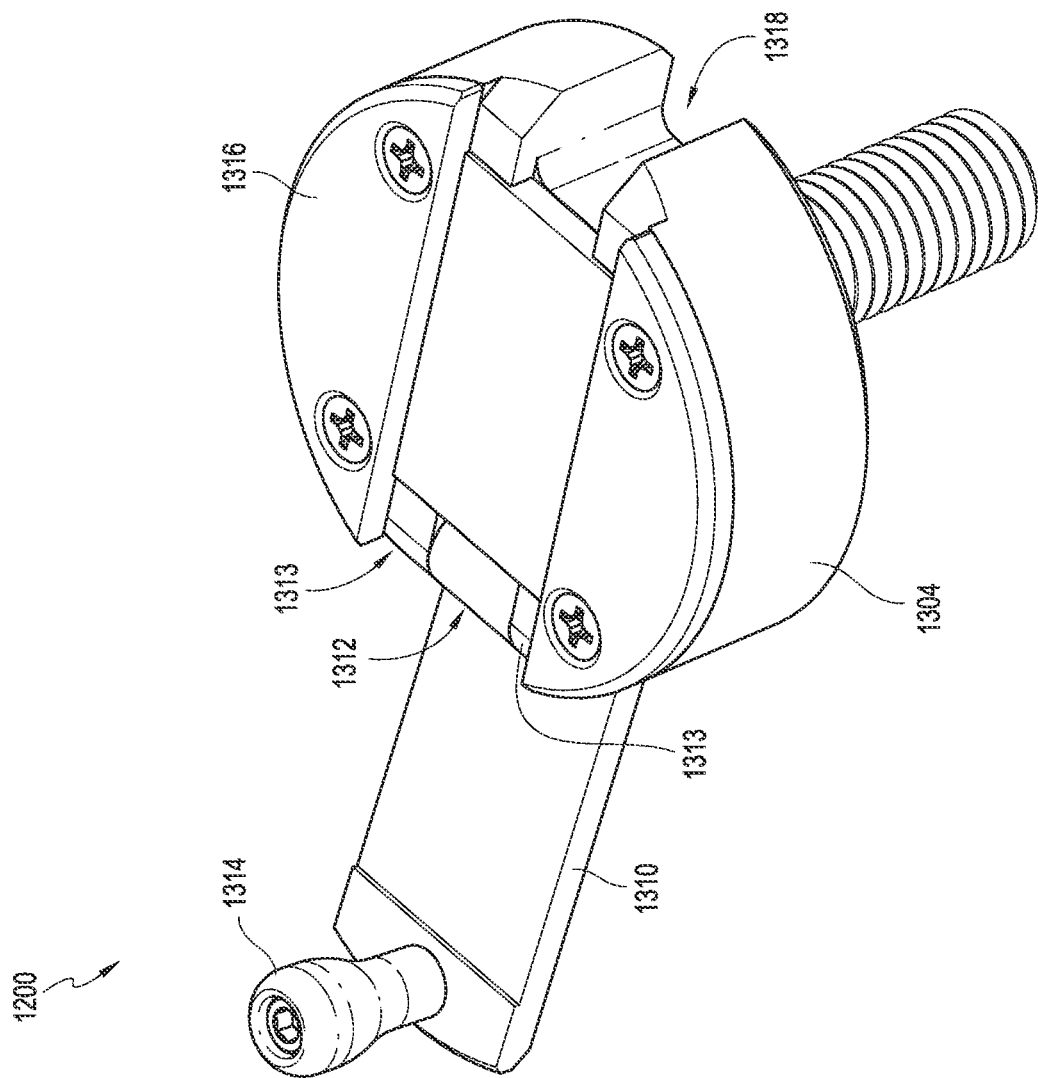

The latch 1310 can include a hollowed portion 1312, which can engage with a pin 1305 located within hollowed portions 1313 of the base 1304 to create a hinge that can couple the latch 1310 and knob 1314 to the base 1304. A user can position the latch 1310 and knob 1314 using the hinge, as desired. For example, in some embodiments, a user can position the latch in a first, or open, position and/or in a second, or closed, position. In the closed position, the knob 1314 can be located within a recess 1318 of the base 1304. In the open position, the latch 1310 can extend away from the base 1304, as illustrated in FIG. 14B.

When in the open position, a user can use the knob 1314 to rotate the latch 1310 and base 1304 about the head of the fastening bolt 1302. Depending on the direction of the rotation, the fastening bolt 1302 can move in an upward or downward direction. As described previously, as the user continues to rotate the base 1304, the fastening bolt 1302 can exert an upward force on the gas canister 132, causing the gas canister to engage with the valve assembly 150 and the piercing pin 158 to puncture the seal of the gas canister 132.

Figure 14C:
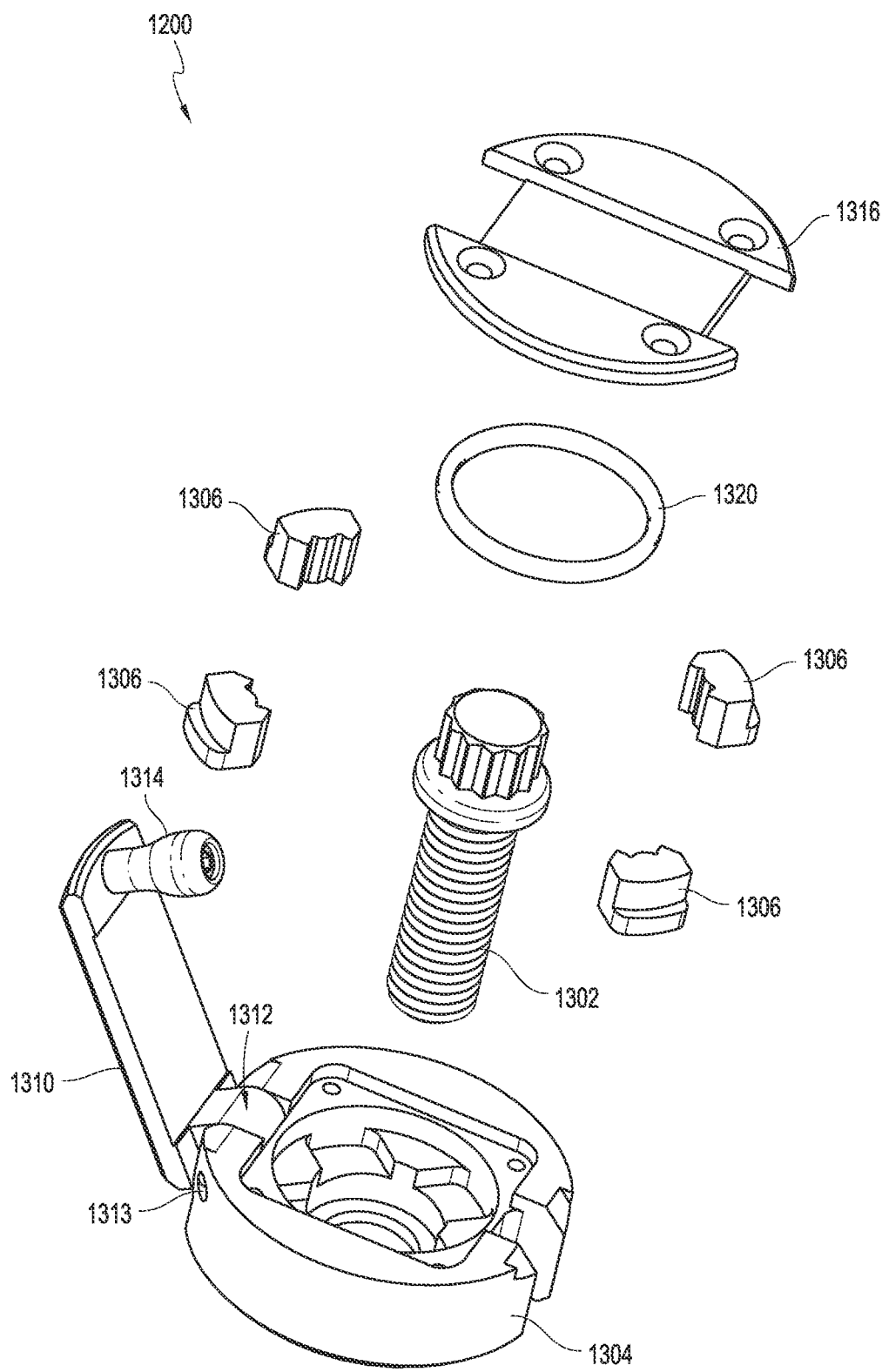
Figure 14D:
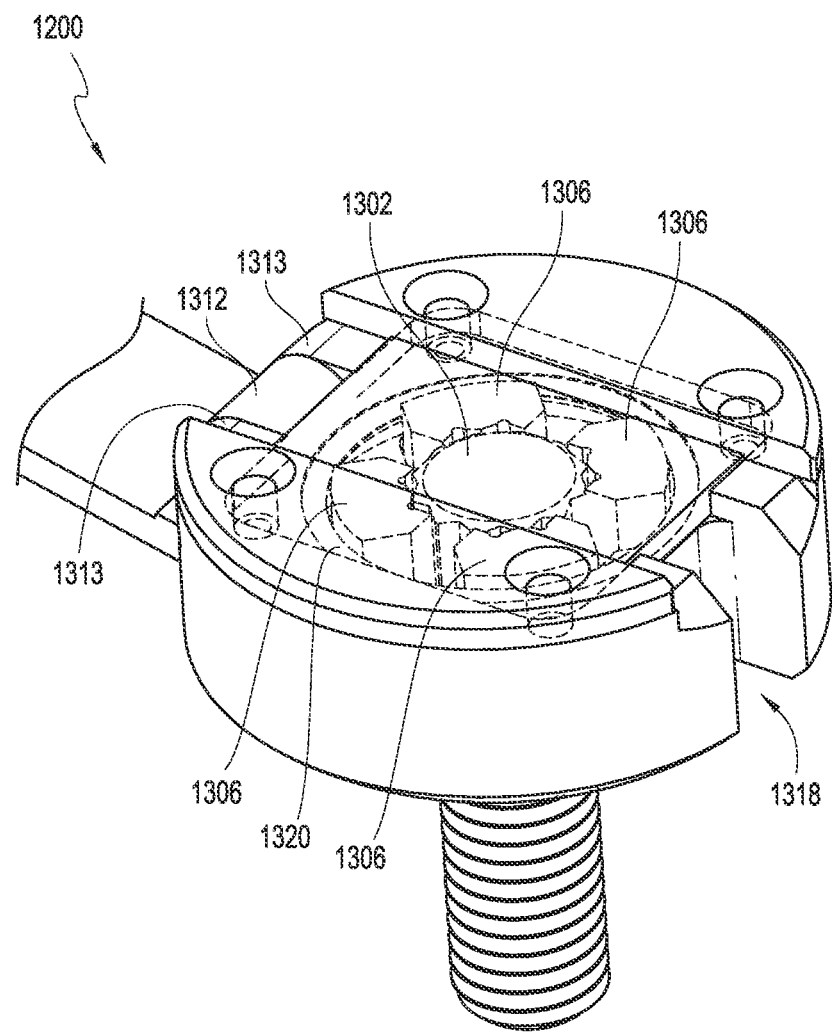

FIGS. 14C and 14D provide different views of drawings of an embodiment of the fastening assembly 1200. FIG. 14C is an exploded view of an embodiment of the fastening assembly 1200, and FIG. 14D is a perspective view showing the placement of components of the fastening assembly 1200 within the base 1304.

In the illustrated embodiments of FIGS. 14C and 14D, the fastening assembly 1200 can include the fastening bolt 1302, the base 1304, the latch 1310, the cover 1316, as well as a torque limiter 1306 and an O-ring 1320, each of which can be made of metal, plastic, rubber, an elastomer, a rigid material, a composite material, or any combination thereof. Although the illustrated embodiment of FIG. 14C shows four components of the torque limiter 1306, it will be understood that any number of components can be used to implement the torque limiter 1306 as desired. For example, in some embodiments, the fastening assembly 1200 can include one or more components as the torque limiter 1306. Furthermore, in certain embodiments, the O-ring 1320 can be considered a component of the torque limiter 1306.

In some embodiments, the O-ring 1320 can be made of rubber, polyethylene, plastic, polymer, propylene, polyurethane, or other elastomer or composite material that is flexible and/or pliable. As illustrated in FIG. 14D, the O-ring 1320 can be located between the torque limiter 1306 and the base 1304. The O-ring 1320 can help keep the torque limiter 1306 in place and/or provide give, or flexibility, to the torque limiter 1306, thereby allowing the torque limiter 1306 to move distally from the head of the fastening bolt 1302. In this way, the head of the bolt 1302 can slip through the torque limiter 1306 once a torque threshold is satisfied.

The torque limiter 1306 can be used to limit the amount of torque that the fastening bolt 1302 exerts on the gas canister 132. For example, in some embodiments, a user can twist the base 1304 until the torque satisfies a torque threshold of the torque limiter 1306. The torque threshold can be set based on the type and configuration of the torque limiter 1306 and/or the flexibility and softness of the O-ring 1320.

Once the torque satisfies the torque threshold, the torque limiter 1306 can prevent or reduce the rotational force exerted by the user to the base 1304 from transferring to the fastening bolt 1302. In this manner, the torque limiter 1306 can prevent or reduce the advancement of the fastening bolt 1302 toward the gas canister 132, despite continued rotation of the base 1304. The torque limiter 1306 can be implemented in a variety of ways. For example, the torque limiter 1306 can be implemented using a shear pin, synchronous magnetic torque limiter, ball detent, pawl and spring, friction plate, magnetic particle, magnetic hysteresis, etc.

In the illustrated embodiments of FIGS. 14C and 14D, as a user continues to twist the base 1304 after the torque satisfies the torque threshold, the protrusions on the head of the fastening bolt 1302 can slip past, or through, the indentations and/or protrusions of the torque limiter 1306. For example, in some embodiments, once the torque threshold is satisfied, any additional rotational force applied to the base 1304 can cause the torque limiter 1306 to move distally from the head of the fastening bolt 1302.

Valve Assembly Embodiments

Figure 15A:
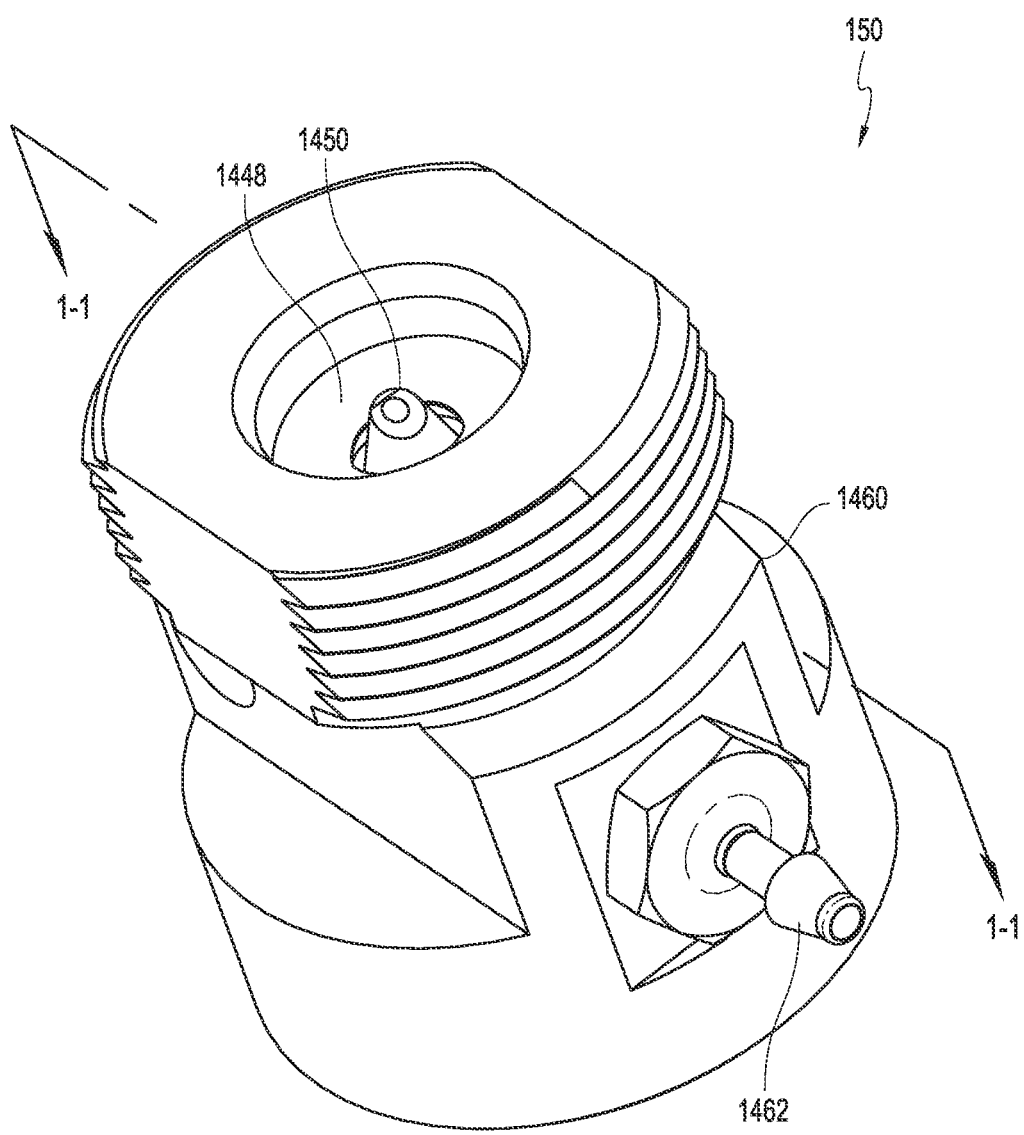
FIGS. 15A-15E are diagrams illustrative of various views of an embodiment of a valve assembly.
Figure 15B:
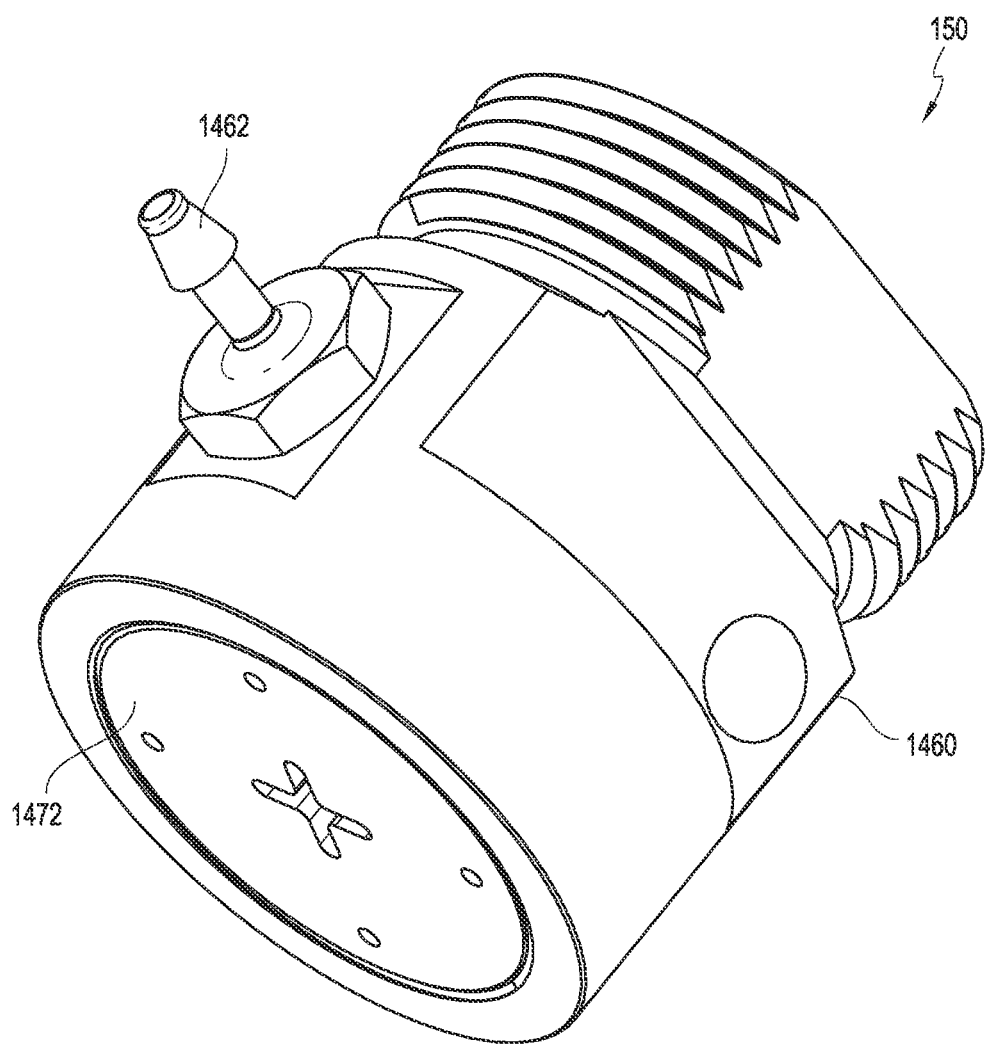
Figure 15C:
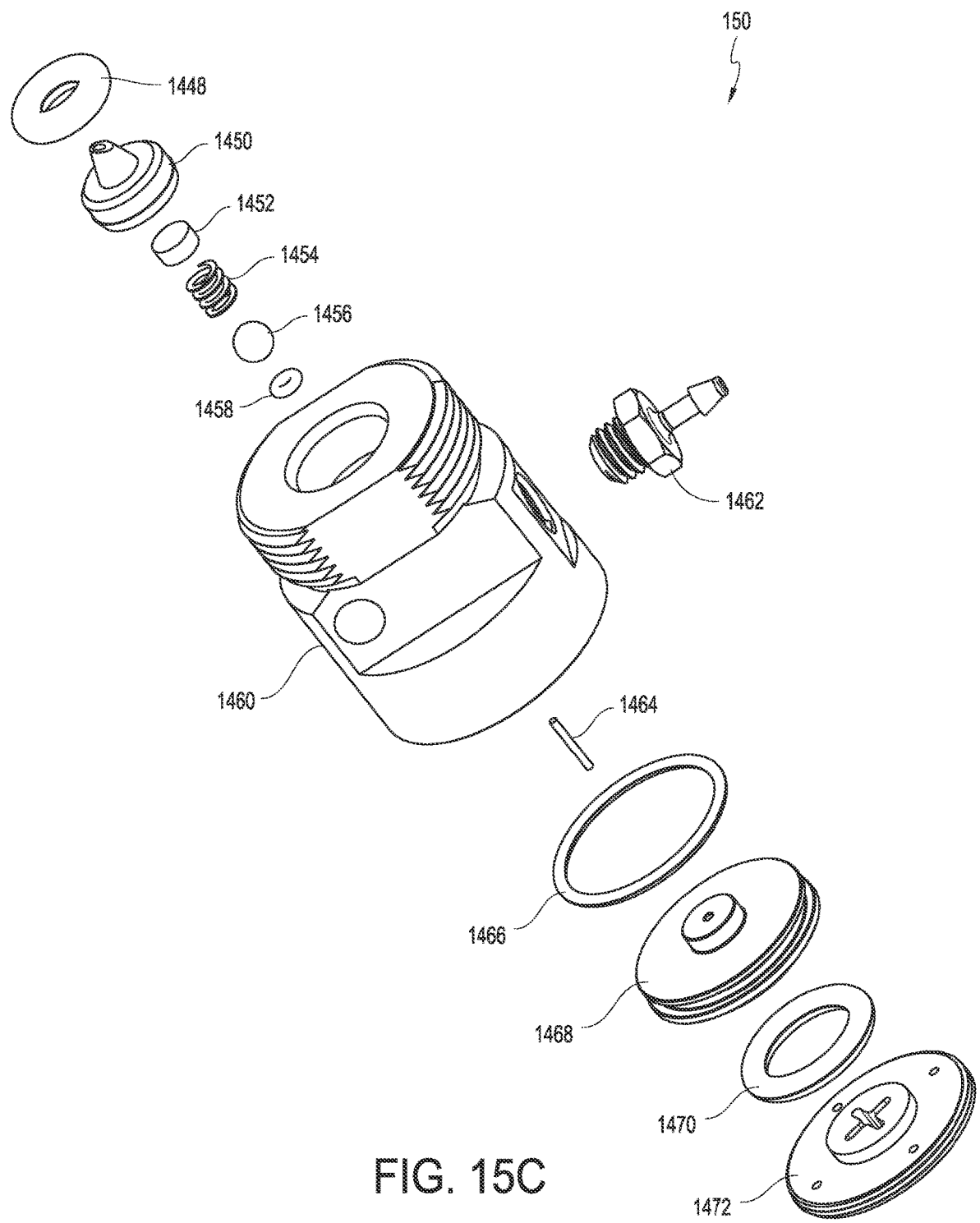
Figure 15D:
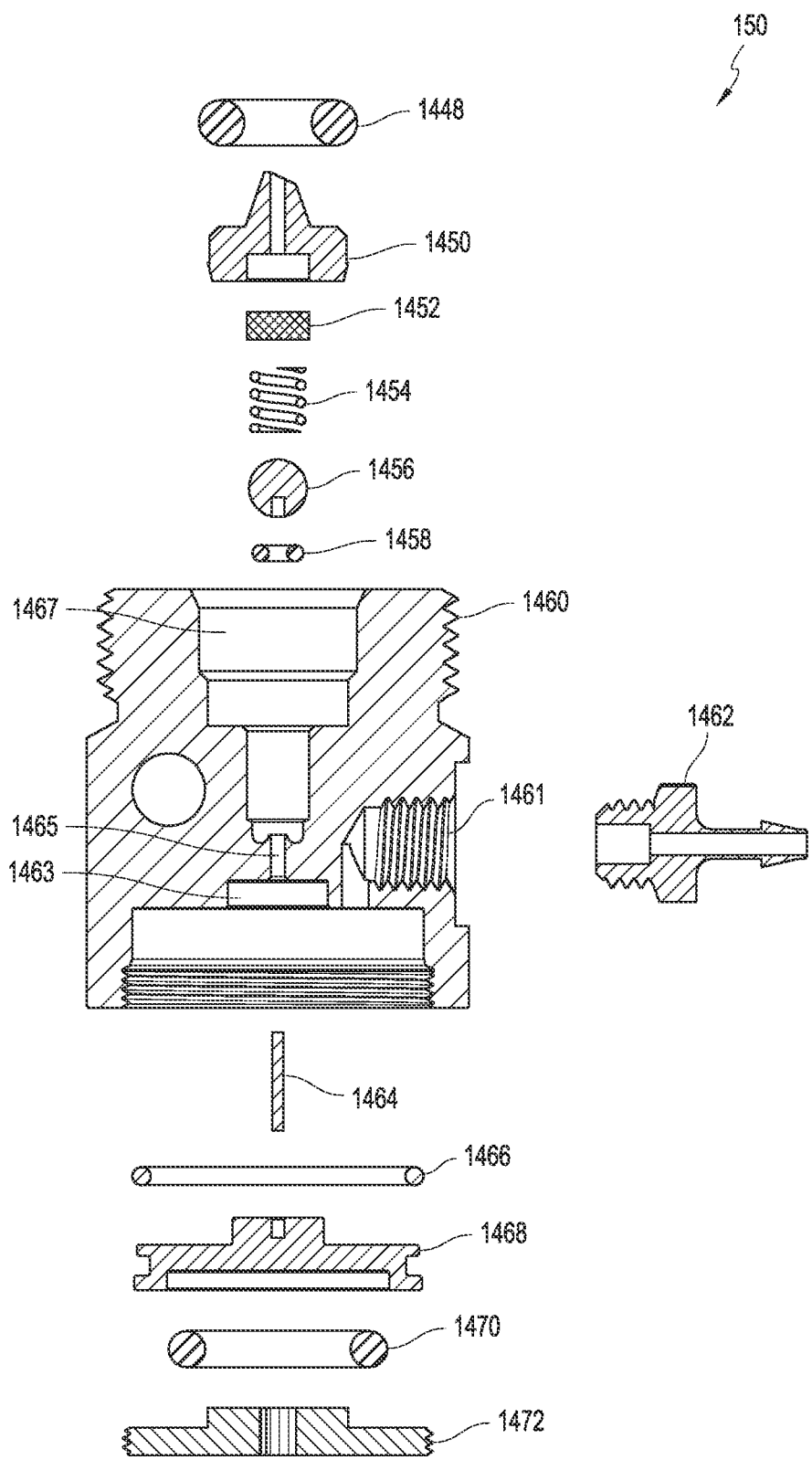
Figure 15E:
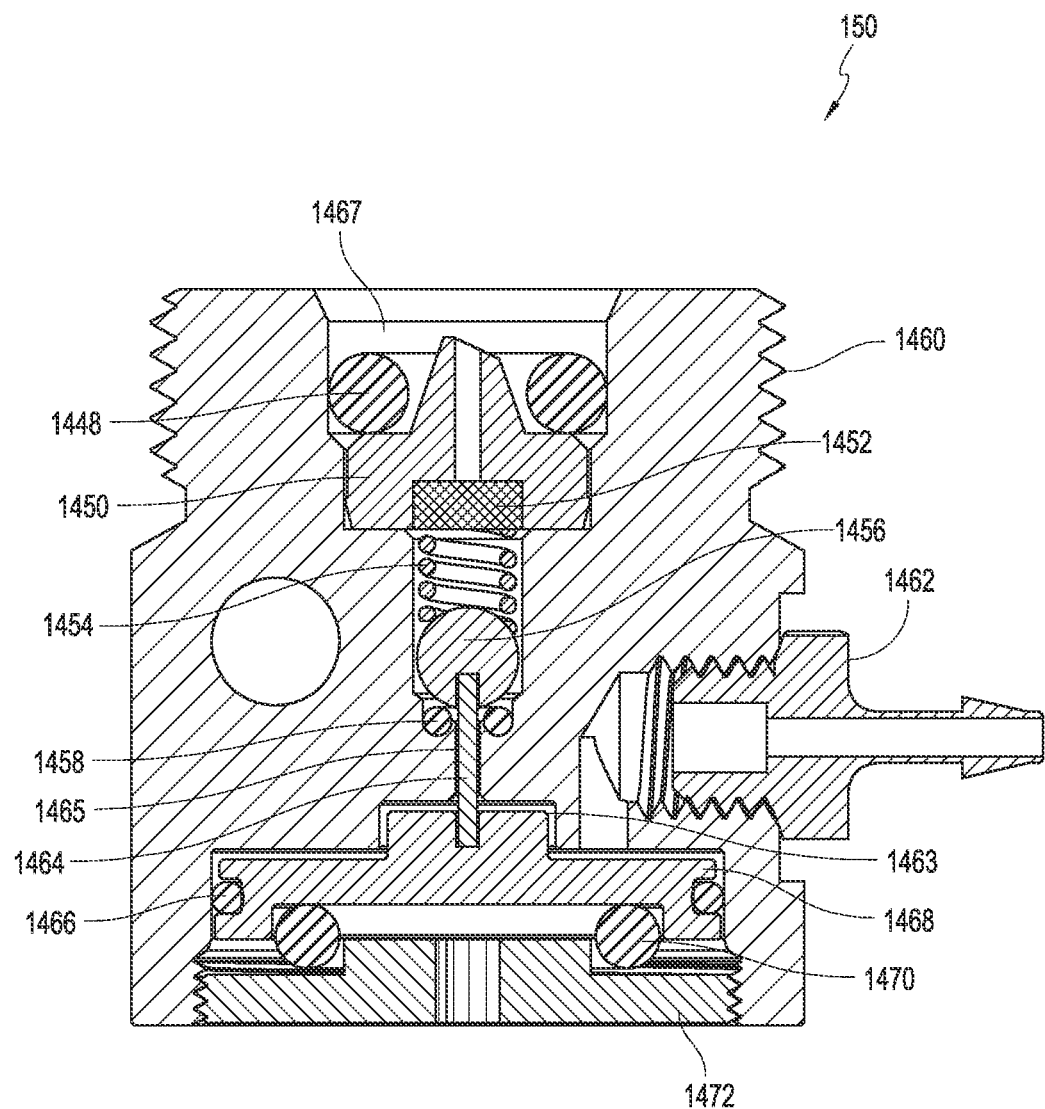

FIGS. 15A-15E are diagrams of various views of another embodiment of a valve assembly 150, which can be implemented with the chamber assembly 102, described above and/or the chamber 306 described in the '225 application. FIGS. 15A and 15B are diagrams of perspective views of the valve assembly 150. FIG. 15C is a diagram of an exploded view of the valve assembly 150. FIG. 15D is a diagram of an exploded cross-sectional view of the valve assembly 150 along the line 1-1 shown in FIG. 15A. FIG. 15E is a diagram of a cross-sectional view of the valve assembly 150 along the line 1-1 shown in FIG. 15A.

In the illustrated embodiments of FIGS. 15A-15E, the valve assembly 150 can include pressure rings 1448, 1458, 1466, 1470, a piercing pin 1450, a filter 1452, a spring 1454, a channel cover 1456, a valve 1460, output nozzle (or output port) 1462, a rod 1464, a cap 1468, and a valve cover 1472, each of which can be made of metal, plastic, rubber, an elastomer, a rigid material, a composite material, or any combination thereof. For example, in some embodiments, the pressure rings 1448, 1458, 1466, 1470, channel cover 1456, and output nozzle (or output port) 1462, can be made of rubber, polyethylene, plastic, polymer, propylene, polyurethane, or other elastomer or composite material that is flexible, pliable, and/or can create a seal between two or more parts. In certain embodiments, the piercing pin 1450, spring 1454, channel cover 1456, valve 1460, output nozzle (or output port) 1462, rod 1464, cap 1468, and valve cover 1472 can be made of metal, plastic, a rigid material, a composite material, or any combination thereof. Furthermore, although illustrated as a circular shape in the illustrated embodiments, it will be understood that the pressure rings 1448, 1458, 1466, 1470, piercing pin 1450, filter 1452, spring 1454, channel cover 1456, valve 1460, output nozzle (or output port) 1462, rod 1464, cap 1468, and valve cover 1472 can be implemented using a variety of shapes, such as rectangular, square, trapezoidal, ellipsoidal, etc.

The valve cover 1472 can be used to protect the components of the valve assembly 150. When assembled, a number of the components of the valve assembly 150 can be located within a cavity of the valve and covered by the valve cover 1472, as illustrated in FIG. 15E. The valve cover 1472 can also be used to configure the valve assembly 150 for a desired pressure level (e.g., a desired pounds per square inch (PSI) level) or pressure level range, as will be described in greater detail below.

The valve 1460 can be used to convert high pressure gas from the gas canister 132 to a lower pressure, and can be made of metal, plastic, a rigid material, a composite material, or any combination thereof. In addition, the valve can house several components of the valve assembly 150 within its cavities. In some embodiments, the valve 1460 can be threaded on one or multiple ends (on the interior or exterior) in order to engage with the chamber assembly 102 and/or the valve cover 1472. In certain embodiments, screws and/or bolts can be used to couple the valve 1460 to the chamber assembly.

The valve 1460 can include inter alia a low pressure cavity 1463 that is distally located from the chamber assembly 102, a high pressure cavity 1467 that is proximally located from the chamber assembly 102, and a high/low pressure channel 1465 that provides a gas pathway between the two cavities 1463, 1467. The valve 1460 can also include an output channel 1461 that engages with the output nozzle 1462. The output nozzle 1462 can be hollow to allow gas to flow through it to an end point.

The piercing pin 1450 and the pressure ring 1448, such as an O-ring, can be located within the high pressure cavity 1467 of the valve 1460 and interface with the seal of the gas canister 1432, as is described in greater detail above with reference to the piercing pin 158 and pressure ring 156 of FIGS. 2-10.

In addition, a filter 1452, spring 1454, channel cover 1456, and pressure ring 1458, can be located within the high pressure cavity 1467. The filter 1452 can be used to reduce the likelihood of particles in the gas canister 132 entering the valve 160, and can be made of a fibrous material.

The spring 1454 can be used to exert an upward force on the channel cover 1456 and the pressure ring 1458. In this manner, the channel cover 1456 and the pressure ring 1458 can create a seal between the high/low pressure channel 1465 and the high pressure cavity 1467. Furthermore, pressurized gas from the gas canister 132 can provide additional force against the channel cover 1456 and pressure ring 1458 to maintain the seal between the high/low pressure channel 1465 and the high pressure cavity 1467, making it more difficult for gas from the gas canister 132 to enter the low pressure cavity 1463. Although illustrated as a spherical shape in the illustrated embodiment, it will be understood that the channel cover 1456 can be implemented using a variety of shapes, such as a pyramid, prism, ellipsoid, spheroid, etc.

A rod 1464 can extend from the low pressure cavity 1463 to the high pressure cavity 1467 through the high/low pressure channel 1465. In some embodiments, the end of the rod 1464 that is proximal to the chamber assembly 102 can engage with the channel cover 1456 via a recess in the channel cover 1456. In certain embodiments, the end of the rod 1464 that is distal to the chamber assembly 102 can engage with the cap 1468 via a recess in the cap 1468. In some embodiments, the rod 1464 and recesses of the channel cover 1456 and cap 1468 can be threaded in order to couple together in a more secure manner. Although in the illustrated embodiment the rod 1464 is shown as a cylinder, it will be understood that the rod 1464 can be implemented as any number of different shapes, such as a prism (e.g., rectangular prism, hexagonal prism, etc.).

The pressure ring 1466 (e.g., an O-ring) can encircle at least a portion of the cap 1468 to prevent gas leakage from the low pressure cavity 1463. The pressure ring 1470 can act as a buffer between the rod 1464 and the valve cover 172 to prevent damage, as well as provide give or flexibility to the cap 1468.

When the valve assembly 150 is assembled, the spring 1454 can exert an upward force against the channel cover 1456 and pressure ring 1458 to create an airtight, or substantially airtight seal between the high pressure cavity 1467 and the high/low pressure channel 1465. However, as mentioned previously, using the valve cover 1472, a gas pathway between the high pressure cavity 1467 and the high/low pressure channel 1465 can be opened.

To open the gas pathway, the valve cover 1472 can be positioned such that a downward force is exerted against the cap 1468 and the bar 1464. In response, the bar 1464 can exert a downward force against the channel cover 1456. Once the downward force exerted by the bar 1464 exceeds the upward force exerted against the channel cover 1456 (e.g., due to the spring 1454 and any pressurized gas in the high pressure cavity 1467, etc.), the channel cover 1456 moves downward opening a gas pathway between the high pressure cavity 1467 and the high/low pressure channel 1465.

Once the gas pathway between the high pressure cavity 1467 and the high/low pressure channel 1465 is opened, the gas in the high pressure cavity 1467 can travel through the high/low pressure channel 1465 and into the low pressure cavity 1463. As the gas travels from the high pressure cavity 1467 to the low pressure cavity 1463, its pressure can change. In some embodiments, the change in pressure of the gas from the high pressure cavity 1467 to the low pressure cavity 1463 can be based at least on the size of the high/low pressure channel 1465. For the gas in the low pressure cavity 1463, a gas pathway can be provided from the low pressure cavity 1463 to the output channel 1461 based at least on the length of the bar 1464 (e.g., a longer length can result in a larger gas pathway, and a shorter length can result in a smaller gas pathway or no gas pathway).

The size of the gas pathway (and therefore the rate of flow of the gas) between the high pressure cavity 1467 and the high/low pressure channel 1465, or the channel cover 1456 and the valve 1460, can be dependent on at least the size of the gap created by the movement of the channel cover 1456 away from the valve 1460 (e.g., a larger gap leads to a larger gas pathway and/or a larger gas flow rate). The location of the valve cover 1472 can determine the size of the gas pathway by controlling the amount of downward force exerted on the bar 1464. For example, as the valve cover 1472 moves downward it can exert a larger downward force on the cap 1468 and the bar 1464. Accordingly, by slightly adjusting the downward force, or the position of, the valve cover 1472, a user can control the rate of gas flow through the valve 1460. In some embodiments, a user can change the position the valve cover 1472 using a screwdriver, by rotating the valve cover 1472, and/or by exerting a downward force on the valve cover. Similarly, a motor can be used to change the position of the valve cover 1472.

In this way, the valve assembly 150 can be set for a particular gas flow rate (or range) or PSI level (or range). The flow rate and/or PSI level for the valve assembly 150 can be set during manufacturing or onsite. Furthermore, using this configuration, the flow rate and/or PSI level can stay approximately constant until the gas canister is empty. In some embodiments, a user can set and/or change the flow rate or PSI output. In certain embodiments, a motor can set and/or change the flow rate or PSI output.

In some embodiments, the flow rate and/or pressure (e.g., PSI level) exiting the valve assembly 150 can increase slightly as the pressure in the gas canister 132 decreases. In such embodiments, the increase in flow rate and/or pressure can be used to determine that the gas canister 132 should be replaced. For example, a pressure sensor, such as the pressure sensors described in the '225 application, previously incorporated herein, can be located in the valve assembly 150 or in a gas pathway. The pressure sensor can sense the pressure of the air exiting the valve assembly 150 and transmit the data to a controller. Once the controller determines that the flow rate and/or pressure exiting the valve assembly 150 satisfies a threshold level, a notice, or alarm, can be triggered indicating that the gas canister 132 should be replaced.

NON-LIMITING EXAMPLE EMBODIMENTS

Various non-limiting example embodiments of the disclosure can be described in view of the following clauses:

Clause 1. A valve-chamber assembly, comprising:
 a bar lever;
 a valve comprising a high pressure cavity, a low pressure cavity, a first channel providing a gas pathway between the high pressure cavity and the low pressure cavity, and a second channel providing a gas pathway between the low pressure cavity and a valve output;
 a piston proximate to the bar lever exerting an upward force on the bar lever and located within the low pressure cavity to create a seal between the first channel and the second channel;
 a motor including an engagement portion that rotates about an axis; and
 an actuator screw comprising
  a first portion engaged with the engagement portion of the motor, and
  a second portion engaged with the bar lever, wherein rotation of the engagement portion of the motor in a first direction causes the actuator screw to exert a force against the bar lever allowing the bar lever and the piston to move distally from the channel and providing a gas pathway between the first channel and the second channel.

Clause 2. A valve-chamber assembly, comprising:
 a bar lever;
 a valve comprising a high pressure cavity, a low pressure cavity, and a channel providing a gas pathway between the high pressure cavity and the low pressure cavity;
 a piston proximate to the bar lever and located within the low pressure cavity to create a seal between the channel and at least a portion of the low pressure cavity;
 a motor including an engagement portion; and
 an actuator comprising:
  a first portion engaged with the engagement portion of the motor, and
  a second portion engaged with the bar lever, wherein a first movement of the motor causes the actuator to exert a force against the bar lever in a first direction allowing the bar lever and the piston to move distally from the channel.

Clause 3. The valve-chamber assembly of clause 2, wherein the low pressure cavity comprises pressurized gas that exerts a force against the piston in the first direction.

Clause 4. The valve-chamber assembly of clause 3, wherein the high pressure cavity comprises pressurized gas having a higher pressure than the pressurized gas in the low pressure cavity.

Clause 5. The valve-chamber assembly of any of clauses 2-4, wherein movement of the piston distally from the channel provides a gas pathway between the channel and an output of the valve.

Clause 6. The valve-chamber assembly of clause 5, wherein a second movement of the motor causes the actuator to reduce the force exerted against the bar lever and allows the piston to move proximally to the channel thereby closing the gas pathway between the channel and the output of the valve.

Clause 7. The valve-chamber assembly of any of clauses 2-6, further comprising a pressure ring encircling at least a portion of the piston and located between the piston and a wall of the low pressure cavity, wherein the pressure ring provides a seal between the piston and the wall of the low pressure cavity.

Clause 8. The valve-chamber assembly of any of clauses 2-7, wherein the channel is a first gas channel, the valve-chamber assembly further comprising a locking assembly, the locking assembly comprising:
 a pin including a head and an elongated portion, the pin located within a pin cavity of a base of the valve-chamber assembly;
 a spring encircling at least a portion of the elongated portion of the pin and exerting a force against the pin in the first direction;
 a receiving cavity located within a cover of the valve-chamber assembly;
 a second gas channel extending from the pin cavity to the valve, wherein pressurized gas from the second gas channel exerts a force against the pin in a second direction sufficient to overcome the force of the spring and causing the pin to engage with the receiving cavity.

Clause 9. The valve-chamber assembly of any of clauses 2-8, further comprising a valve protection circuit, the valve protection circuit comprising:
 a plurality of registers configured to monitor a status of a plurality of safety parameters;
 a plurality of buffers configured to regulate communication pathways between a plurality of control signals and the motor; and
 a super capacitor, wherein
 the plurality of buffers disable the communication pathways between the plurality of control signals and the motor when the status of any one of the plurality of monitored safety parameters does not satisfy a threshold status, and wherein
 the super capacitor discharges and causes the actuator to move in a second direction that is substantially opposite the first direction when the status of any one of the plurality of monitored safety parameters does not satisfy a threshold status.

Clause 10. The valve-chamber assembly of clause 9, wherein the monitored safety parameters comprise electrical power, a refresh signal, and a safety signal.

Clause 11. The valve-chamber assembly of any of clauses 9 and 10, wherein the plurality of control signals comprise a pulse-width modulated signal, an open/close signal, and an enable signal.

Clause 12. A method for controlling the flow of gas in a valve-chamber assembly, the method comprising:
 providing a bar lever;

providing a valve comprising a high pressure cavity, a low pressure cavity, a channel providing a gas pathway between the high pressure cavity and the low pressure cavity, wherein the low pressure cavity comprises pressurized gas exerting a force against the piston in a first direction;

providing a seal between the channel and at least a portion of the low pressure cavity using a piston proximate to the bar lever and located within the low pressure cavity;

actuating an actuator engaged with the bar lever in the first direction, wherein the actuator exerts a force against the bar lever in the first direction thereby providing a gas pathway between the channel and a valve output; and actuating the actuator in a second direction to close the gas pathway between the channel and the valve output.

Clause 13. The method of clause 12, wherein the low pressure cavity comprises pressurized gas that exerts a force against the piston in the first direction.

Clause 14. The method assembly of clause 13, wherein the high pressure cavity comprises pressurized gas having a higher pressure than the pressurized gas in the low pressure cavity.

Clause 15. The method of any of clauses 12 and 13, wherein movement of the piston distally from the channel provides a gas pathway between the channel and an output of the valve.

Clause 16. The method of clause 15, wherein a second movement of the motor causes the actuator to reduce the force exerted against the bar lever and allows the piston move proximally to the channel thereby closing the gas pathway between the channel and the output of the valve.

Clause 17. The method of any of clauses 12-16, further comprising a pressure ring encircling at least a portion of the piston and located between the piston and a wall of the low pressure cavity, wherein the pressure ring provides a seal between the piston and the wall of the low pressure cavity.

Clause 18. The method of any of clauses 12-17, wherein the channel is a first gas channel and the method further comprises:

providing a pin including a head and an elongated portion within a pin cavity of a base of the valve-chamber assembly;

providing a spring that encircling at least a portion of the elongated portion of the pin and exerts a force against the pin in the first direction; and exerting a force against the pin in a second direction that is substantially opposite the first direction using pressurized gas from the valve, wherein the force against the pin is greater than the force of the spring in the first direction.

Clause 19. The method of any of clauses 12-18, further comprising closing the gas pathway between the channel and the valve output in response to a determination that at least one monitored safety parameter does not satisfy a threshold status.

Clause 20. The method of any of clauses 12-19, wherein the at least one monitored safety parameter comprises at least one of electrical power, a refresh signal, and a safety signal.

Clause 21. A blood pressure measurement system, comprising:

an inflatable cuff configured to encompass a limb of a patient;

a chamber assembly configured to house a gas canister having gas for inflating the inflatable cuff;

a valve assembly coupled to the chamber assembly; and a gas pathway between the valve assembly and the inflatable cuff, wherein the valve assembly includes:

a valve comprising a high pressure cavity, a low pressure cavity, a first channel providing a gas pathway between the high pressure cavity and the low pressure cavity, and a second channel providing a gas pathway between the low pressure cavity and a valve output, a channel cover and a pressure ring located within the high pressure cavity, a spring exerting an upward force on the channel cover and the pressure ring to create a seal between the high pressure cavity and the first channel, and a rod extending from the low pressure cavity to the high pressure cavity via the first channel and exerting a downward force on the channel cover to provide a gas pathway between the high pressure cavity and the first channel.

Clause 22. The blood pressure measurement system of clause 21, wherein the chamber assembly comprises:

a housing including a base that is distal to the valve assembly, wherein the housing is configured to house the gas canister;

a bolt extending through an open portion of the base; and a torque limiter located within the base and at least partially surrounding a head of the bolt, wherein if a torque threshold is not satisfied, rotational movement of the base in a first direction causes the bolt to rotate in the first direction and advance towards the gas canister, and wherein if the torque threshold is satisfied, rotational movement of the base in a first direction causes the head of the bolt to slip through the torque limiter.

Clause 23. A valve-chamber assembly, comprising:

a valve comprising a high pressure cavity, a low pressure cavity, a first channel providing a gas pathway between the high pressure cavity and the low pressure cavity, and a second channel providing a gas pathway between the low pressure cavity and a valve output;

a channel cover and a pressure ring located within the high pressure cavity;

a spring exerting an upward force on the channel cover and the pressure ring to create a first seal between the high pressure cavity and the first channel; and a rod extending from the low pressure cavity to the high pressure cavity via the first channel and exerting a downward force on the channel cover to provide a gas pathway between the high pressure cavity and the first channel.

Clause 24. The valve-chamber assembly of clause 23, further comprising a cap exerting a downward force on the rod.

Clause 25. The valve-chamber assembly of clause 24, further comprising an O-ring encircling at least a portion of the cap and located between the cap and a wall of the low pressure cavity, wherein the O-ring provides a second seal between the cap and the wall of the low pressure cavity.

Clause 26. The valve-chamber assembly of any of clauses 24 and 25, further comprising a valve cover exerting a downward force on the cap.

Clause 27. The valve-chamber assembly of clause 25, wherein downward movement of the valve cover results in an increased gas pressure at the valve output.

Clause 28. The valve-chamber assembly of any of clauses 23-26, further comprising a piercing pin coupled with the spring to pierce a gas canister seal.

Clause 29. The valve-chamber assembly of clause 27, further comprising a base with a gas canister residing therein.

Clause 30. The valve-chamber assembly of clause 28, further comprising a second pressure ring coupled with the piercing pin and an upper portion of the gas canister to provide a second seal between the high pressure cavity and an exterior of the valve.

Clause 31. The valve-chamber assembly of any of clauses 23-29, wherein the high pressure cavity comprises pressurized gas having a higher pressure than pressurized gas in the low pressure cavity.

Clause 32. The valve-chamber assembly of any of clauses 23-31, further comprising:
a base;
a bolt fitted through an open portion of the base;
a torque limiter located within the base and at least partially surrounding a head of the bolt;
an O-ring located between at least a portion of the torque limiter and the base; and
wherein if a torque threshold is not satisfied, rotational movement of the base in a first direction causes the bolt to rotate in the first direction and advance towards the gas canister, and
wherein if the torque threshold is satisfied, rotational movement of the base in the first direction causes the head of the bolt to slip through the torque limiter.

Clause 33. A blood pressure measurement system, comprising:
an inflatable cuff configured to encompass a limb of a patient;
a valve-chamber assembly configured to house a gas canister; and
a gas pathway between the valve-chamber assembly and the inflatable cuff, wherein the valve-chamber assembly includes:
a base,
a bolt fitted through an open portion of the base,
a torque limiter located within the base and at least partially surrounding a head of the bolt,
an O-ring located between at least a portion of the torque limiter and the base, and
a latch coupled to the base,
wherein if a torque threshold is not satisfied, rotational movement of the latch in a first direction causes the bolt to rotate in the first direction and advance towards the gas canister, and
wherein if the torque threshold is satisfied, rotational movement of the latch in the first direction causes the head of the bolt to slip through the torque limiter.

Clause 34. A valve-chamber assembly having a fastening assembly, the fastening assembly comprising:
a base;
a bolt fitted through an open portion of the base;
a torque limiter located within the base and at least partially surrounding a head of the bolt;
an O-ring located between at least a portion of the torque limiter and the base; and
a latch coupled to the base,
wherein if a torque threshold is not satisfied, rotational movement of the latch in a first direction causes the bolt to rotate in the first direction and advance in a second direction, and
wherein if the torque threshold is satisfied, rotational movement of the latch in the first direction causes the head of the bolt to slip through the torque limiter.

Clause 35. The valve-chamber assembly of clause 34, wherein the rotational movement of the latch causes the bolt to exert a force in the direction of a piercing pin on a gas canister located within a chamber assembly.

Clause 36. The valve-chamber assembly of any of clauses 34 and 35, wherein the latch is hingedly coupled to the base and the latch further comprises a knob.

Clause 37. The valve-chamber assembly of clause 36, wherein in a first position, the knob is located within a recess of the base, and in a second position the knob is used to rotate the base.

Clause 38. The valve-chamber assembly of any of clauses 34-37, wherein based at least on the torque threshold being satisfied, rotational movement of the latch in the first direction causes the torque limiter to move distally from the head of the bolt.

Clause 39. A method for detecting a time to replace a gas canister, the method comprising:
monitoring an output pressure level of a valve;
determining that the output pressure level satisfies a threshold pressure; and
indicating that a corresponding gas canister should be replaced.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

A skilled artisan will appreciate that the configurations and principles of the embodiments can be adapted for any electronic system. The circuits employing the above described configurations can be implemented into various electronic devices or integrated circuits. Furthermore, the various topologies, configurations and embodiments described above may be implemented discretely or integrated on a chip without departing from the spirit and scope of the description.

The foregoing description and claims may refer to elements or features as being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically. Thus, although the various schematics shown in the figures depict example arrangements of elements and components, additional intervening elements, devices, features, or components may be present in an actual embodiment (assuming that the functionality of the depicted circuits is not adversely affected).

Embodiments are also described above with reference to controllers and/or control systems. The control system and/or controllers can be implemented using a processor of a general purpose computer, microprocessor, microcontroller, special purpose computer, or other programmable data processing apparatus (e.g., programmable logic device (PLD), field-programmable gate array (FPGA), and the like). Relevant instructions can be stored in a tangible non-transitory computer-readable medium. Such instructions may be provided to the processor (or other device), such that the instructions, which execute via the processor of the computer or other programmable data processing apparatus, create means for implementing the acts performed by the controller.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded onto a computer or other programmable data processing apparatus to cause a series of operations to be performed on the computer or other programmable apparatus to produce a computer implemented process such that the instructions which execute on the computer or other programmable apparatus provide steps for implementing the acts specified.

Although this disclosure has been described in terms of certain embodiments, other embodiments that are apparent to those of ordinary skill in the art, including embodiments that do not provide all of the features and advantages set forth herein, are also within the scope of the disclosure. Moreover, the various embodiments described above can be combined to provide further embodiments. In addition, certain features shown in the context of one embodiment can be incorporated into other embodiments as well. Accordingly, the scope of the disclosure is defined only by reference to the appended claims.

The invention claimed is:

1. A blood pressure measurement system configured to measure blood pressure of a wearer of an inflatable cuff, the system comprising:
    an inflatable cuff configured to encompass a limb of a patient;
    a chamber assembly configured to receive a gas reservoir;
    a valve assembly coupled to the chamber assembly, wherein the valve assembly includes a valve;
    a gas pathway between the valve assembly and the inflatable cuff; and
    a piston located within the valve of the valve assembly, wherein a flow rate of gas through the gas pathway to the inflatable cuff changes as a location of the piston within the valve changes;
    a bar lever located to restrict movement of the piston in a first direction;
    a motor coupled to an actuator that is coupled to the bar lever, wherein rotation of the motor causes at least a portion of the actuator of extend or retract to vary a location of the bar lever; and
    one or more processors in communication with the motor and configured to:
    receive reservoir pressure data from a pressure sensor associated with the gas reservoir,
    based at least in part on a determination that the reservoir pressure data satisfies a canister replacement threshold, provide an indication to replace or refill the gas reservoir,
    receive cuff pressure data from a pressure sensor associated with the inflatable cuff, and
    based at least in part on a determination that the cuff pressure data falls within a blood pressure measurement range, actuate the motor to move the bar lever in the first direction or a second direction to increase or decrease, respectively, the flow rate of the gas through the gas pathway.

2. The blood pressure measurement system of claim 1, wherein movement of the bar lever in the first direction causes the piston to move in the first direction thereby increasing the flow rate of the gas through the gas pathway.

3. The blood pressure measurement system of claim 1, wherein movement of the bar lever in the second direction causes the piston to move in the second direction thereby decreasing the flow rate of the gas through the gas pathway.

4. The blood pressure measurement system of claim 1, wherein rotation of the motor in a fourth direction causes at least a portion of the actuator to retract causing the bar lever to move in the second direction and exert a force on the piston to move the piston in the second direction.

5. The blood pressure measurement system of claim 1, wherein the one or more processors are further configured to determine a blood pressure measurement of the patient based at least in part on cuff pressure data over a first time interval, wherein the first time interval occurs during inflation of the inflatable cuff.

6. The blood pressure measurement system of claim 1, wherein the one or more processors are further configured to determine a blood pressure measurement of the patient based at least in part on cuff pressure data over a first time interval, wherein the first time interval occurs during deflation of the inflatable cuff.

7. The blood pressure measurement system of claim 1, wherein movement of the piston in the first direction corresponds to an increased distance between the piston and the chamber assembly.

8. The blood pressure measurement system of claim 1, wherein to actuate the motor to move the bar lever in the first direction or the second direction the one or more processors are configured to actuate the motor to move the bar lever in the second direction so as to cause the piston to close the gas pathway.

9. A method of measuring blood pressure of a wearer of an inflatable cuff, the method comprising:
    receiving cuff pressure data from a pressure sensor associated with an inflatable cuff, the inflatable cuff encompassing a limb of a patient and configured to receive gas from a gas reservoir through a gas pathway of a valve, the valve including a piston located within the gas pathway, wherein a flow rate of the gas through the gas pathway to the inflatable cuff changes as a location of the piston within the gas pathway changes;

determining that the cuff pressure data satisfies a blood pressure measurement condition; and based at least in part on said determining, actuating a motor that is coupled to an actuator that is coupled to a bar lever, the bar lever located to restrict movement of the piston in a first direction, wherein actuation of the motor causes at least a portion of the actuator of extend or retract to vary a location of the bar lever;

receiving reservoir pressure data from a pressure sensor associated with the gas reservoir; and based at least in part on a determination that the reservoir pressure data satisfies a canister replacement threshold, providing an indication to replace or refill the gas reservoir.

10. The method of claim 9, wherein movement of the bar lever in the first direction causes the piston to move in the first direction thereby increasing the flow rate of the gas through the gas pathway.

11. The method of claim 9, wherein movement of the bar lever in a second direction causes the piston to move in the second direction thereby decreasing the flow rate of the gas through the gas pathway.

12. The method of claim 9, wherein rotation of the motor in a fourth direction causes at least a portion of the actuator to retract causing the bar lever to move in the second direction and exert a force on the piston to move the piston in the second direction.

13. The method of claim 11, wherein said actuating the motor comprises actuating the motor to move the bar lever in the second direction.

14. The method of claim 13, wherein said actuating the motor to move the bar lever in the second direction so as to cause the piston to close the gas pathway.

15. The method of claim 9, wherein rotation of the motor in a third direction causes at least a portion of the actuator to extend towards and exert a force against the bar lever in the first direction.

16. The method of claim 9, further comprising determining a blood pressure measurement of the patient based at least in part on pressure data over a first time interval, wherein the first time interval occurs during inflation of the inflatable cuff.

17. The method of claim 9, further comprising determining a blood pressure measurement of the patient based at least in part on pressure data over a first time interval, wherein the first time interval occurs during deflation of the inflatable cuff.

18. The method of claim 9, wherein said actuating the motor comprises actuating the motor to move the bar lever in the first direction.

19. The method of claim 9, wherein movement of the piston in the first direction corresponds to an increased distance between the piston and the gas canister.

* * * * *

UNITED STATES PATENT AND TRADEMARK OFFICE
CERTIFICATE OF CORRECTION

PATENT NO. : 12,318,176 B2
APPLICATION NO. : 18/592189
DATED : June 3, 2025
INVENTOR(S) : Cristiano Dalvi et al.

Page 1 of 2

It is certified that error appears in the above-identified patent and that said Letters Patent is hereby corrected as shown below:

On the Title Page

Item (56) In U.S. Patent Documents, under Column no. 1, page 2, Line no. 2, change "Trutt et al." to --Trott et al.--.

Item (56) In U.S. Patent Documents, under Column no. 2, page 4, Line no. 2, change "Al-All et al." to --Al-Ali et al.--.

Item (56) In U.S. Patent Documents, under Column no. 2, page 5, Line no. 37, change "Klani et al." to --Kiani et al.--.

Item (56) In U.S. Patent Documents, under Column no. 2, page 5, Line no. 67, change "Klani et al." to --Kiani et al.--.

Item (56) In U.S. Patent Documents, under Column no. 2, page 7, Line no. 13, change "Klani et al." to --Kiani et al.--.

Item (56) In U.S. Patent Documents, under Column no. 1, page 9, Line no. 30, change "Klani" to --Kiani--.

Item (56) In U.S. Patent Documents, under Column no. 2, page 9, Line no. 56, change "Klant et al." to --Kiani et al.--.

Item (56) In U.S. Patent Documents, under Column no. 2, page 9, Line no. 75, change "Klani et al." to --Kiani et al.--.

In the Specification

Under Column no. 4, Line nos. 17-18, change "titled "Universal Upgrading Pulse" to --"Universal/Upgrading Pulse--.

Signed and Sealed this
Sixteenth Day of September, 2025

Coke Morgan Stewart
*Acting Director of the United States Patent and Trademark Office*

In the Claims

Under Column no. 29, Claim 12, Line no. 28, change "claim 9, wherein" to --claim 11, wherein--.